(12) United States Patent
He

(10) Patent No.: US 11,266,675 B2
(45) Date of Patent: Mar. 8, 2022

(54) METHODS OF TREATMENT OF VIRAL INFECTION AND USES OF ANTI-HSC70 INHIBITORS

(71) Applicant: City University of Hong Kong, Hong Kong (HK)

(72) Inventor: Ming-liang He, Hong Kong (HK)

(73) Assignee: CITY UNIVERSITY OF HONG KONG, Hong Kong (HK)

(*) Notice: Subject to any disclaimer, the term of this patent is extended or adjusted under 35 U.S.C. 154(b) by 365 days.

(21) Appl. No.: 15/966,121

(22) Filed: Apr. 30, 2018

(65) Prior Publication Data
US 2019/0328760 A1 Oct. 31, 2019

(51) Int. Cl.
*A61K 31/70* (2006.01)
*A61K 31/7076* (2006.01)
*A61K 31/7105* (2006.01)
*C12N 15/113* (2010.01)
*A61P 31/14* (2006.01)

(52) U.S. Cl.
CPC ...... *A61K 31/7076* (2013.01); *A61K 31/7105* (2013.01); *A61P 31/14* (2018.01); *C12N 15/1131* (2013.01); *C12N 2310/14* (2013.01)

(58) Field of Classification Search
CPC .................................................. A61K 31/7076
USPC .......................................................... 514/45
See application file for complete search history.

(56) References Cited

U.S. PATENT DOCUMENTS

| 2009/0156473 | A1* | 6/2009 | Schubert | A61K 31/325 514/1.1 |
| 2013/0190345 | A1* | 7/2013 | Jiang | A61P 31/20 514/288 |
| 2015/0366892 | A1* | 12/2015 | Wang | A61P 35/00 536/27.6 |

OTHER PUBLICATIONS

Taguwa et al. "Defining Hsp70 subnetworks in Dengue virus replication reveals key vulnerability in flavivirus infection," Cell, 2015, vol. 163, pp. 1108-1123. (Year: 2015).*
Khachatoorian et al. "Allosteric heat shock protein 70 inhibitors block hepatitis C virus assembly," International J. Antimicrobial Agents, 2016, vol. 47, pp. 289-296. (Year: 2016).*
Tsou et al. "Heat shock protein 90: role in enterovirus 71 entry and assembly and potential target for Therapy," PLOS One, 2013 vol. 8, No. 10, e77133 (Year: 2013).*
Massey et al. "A novel, small molecule inhibitor of Hsc70/Hsp70 potentiates Hsp90 inhibitor induced apopotosis in HCT116 colon carcinoma cells," Cancer Chemother. Pharmacol. 2010, vol. 66, pp. 535-545 (Year: 2010).*
PubChem CID 25195348 (Year: 2009).*
Badorff, C., Lee, G.H., Lamphear, B.J., Martone, M.E., Campbell, K.P., Rhoads, R.E., Knowlton, K.U., 1999. Enteroviral protease 2A cleaves dystrophin: evidence of cytoskeletal disruption in an acquired cardiomyopathy. Nature medicine 5, 320-326.
Böcking, T., Aguet, F., Harrison, S.C., Kirchhausen, T., 2011. Single-molecule analysis of a molecular disassemblase reveals the mechanism of Hsc70-driven clathrin uncoating Nat Struct Mol Biol 18, 295-301.

(Continued)

*Primary Examiner* — Shengjun Wang
(74) *Attorney, Agent, or Firm* — Heslin Rothenberg Farley & Mesiti, P.C.

(57) ABSTRACT

There are disclosed methods of treatment of viral infection. The method makes use of administration of an anti-Hsc70 inhibitor. There are also disclosed uses of anti-Hsc70 inhibitor.

3 Claims, 23 Drawing Sheets

Specification includes a Sequence Listing.

(56) References Cited

OTHER PUBLICATIONS

Chang, L.-y., Lin, T.-y., Huang, Y.-c., Tsao, K.-c., Shih, S.-r., Kuo, M.-I., Ning, H.-c., Chung, P.-w., Kang, C.-m., 1999. Comparison of enterovirus 71 and coxsackievirus A16 clinical illnesses during the Taiwan enterovirus epidemic, 1998. The Pediatric Infectious Disease Journal 18, 1092-1096. (Abstract only).
Chen, L.L., Kung, Y.A., Weng, K.F., Lin, J.Y., Horng, J.T., Shih, S.R., 2013. Enterovirus 71 infection cleaves a negative regulator for viral internal ribosomal entry site-driven translation. J Virol 87, 3828-3838.
Chuang, C.-K., Yang, T.-H., Chen, T.-H., Yang, C.-F., Chen, W.-J., 2015. Heat shock cognate protein 70 isoform D is required for clathrin-dependent endocytosis of Japanese encephalitis virus in C6/36 cells. Journal of General Virology 96, 793-803.
Chung, S.-K., Kim, J.-Y., Kim, I.-B., Park, S.-I., Paek, K.-H., Nam, J.-H., 2005. Internalization and trafficking mechanisms of coxsackievirus B3 in HeLa cells. Virology 333, 31-40.
Dong, Qi, Ruotin Men, Xuelian Dan, Ying Chen, Huangcan Li, Gong Chen, Benny Zee, Maggie H.T. Wang, Ming-Liang He, 2018. HSC70 regulates the IRES activity and serves as an antiviral target of enterovirus A71 infection, Antiviral Research 150, 39-46.
Duan, H., Zhu, M., Xiong, Q., Wang, Y., Xu, C., Sun, J., Wang, C., Zhang, H., Xu, P., Peng, Y., 2017. Regulation of enterovirus 2A protease-associated viral IRES activities by the cell's ERK signaling cascade: Implicating ERK as an efficiently antiviral target. Antiviral Res 143, 13-21.
Gao, M., Duan, H., Liu, J., Zhang, H., Wang, X., Zhu, M., Guo, J., Zhao, Z., Meng, L., Peng, Y., 2014. The multi-targeted kinase inhibitor sorafenib inhibits enterovirus 71 replication by regulating IRES-dependent translation of viral proteins. Antiviral research 106, 80-85.
Ho , M., Chen , E.-R., Hsu , K.-H., Twu , S.-J., Chen , K.-T., Tsai, S.-F., Wang , J.-R., Shih , S.-R., 1999. An Epidemic of Enterovirus 71 Infection in Taiwan. New England Journal of Medicine 341, 929-935.
Hu, J.J., Song, W., Zhang, S.D., Shen, X.H., Qiu, X.M., Wu, H.Z., Gong, P.H., Lu, S., Zhao, Z.J., He, M.L., Fan, H., 2016. HBx-upregulated lncRNA UCA1 promotes cell growth and tumorigenesis by recruiting EZH2 and repressing p27Kip1/CDK2 signaling. Scientific reports 6, 23521.
Huang, H.I., Chang, Y.Y., Lin, J.Y., Kuo, R.L., Liu, H.P., Shih, S.R., Wu, C.C., 2016. Interactome analysis of the EV71 5' untranslated region in differentiated neuronal cells SH-SY5Y and regulatory role of FBP3 in viral replication. Proteomics 16, 2351-2362.
Huang, H.-I., Weng, K.-F., Shih, S.-R., 2012. Viral and host factors that contribute to pathogenicity of enterovirus 71. Future microbiology 7, 467-479.
Huang , C.-C., Liu , C.-C., Chang , Y.-C., Chen , C.-Y., Wang , S.-T., Yeh , T.-F., 1999. Neurologic Complications in Children with Enterovirus 71 Infection. New England Journal of Medicine 341, 936-942.
Hung, C.-T., Kung, Y.-A., Li, M.-L., Brewer, G., Lee, K.-M., Liu, S.-T., Shih, S.-R., 2016. Additive promotion of viral internal ribosome entry site-mediated translation by Far Upstream Element-Binding Protein 1 and an Enterovirus 71-induced cleavage product. PLoS pathogens 12, e1005959.
Hunt, S.L., Skern, T., Liebig, H.D., Kuechler, E., Jackson, R.J., 1999. Rhinovirus 2A proteinase mediated stimulation of rhinovirus RNA translation is additive to the stimulation effected by cellular RNA binding proteins. Virus research 62, 119-128.
Jheng, J.-R., Wang, S.-C., Jheng, C.-R., Horng, J.-T., 2016. Enterovirus 71 induces dsRNA/PKR-dependent cytoplasmic redistribution of GRP78/BiP to promote viral replication. Emerging microbes & infections 5, e23.
Kung, Y.A., Hung, C.T., Chien, K.Y., Shih, S.R., 2017. Control of the negative IRES trans-acting factor KHSRP by ubiquitination. Nucleic Acids Res 45, 271-287.

Lee, K.M., Chen, C.J., Shih, S.R., 2017. Regulation Mechanisms of Viral IRES-Driven Translation. Trends in microbiology 25, 546-561.
Lin, J.-Y., Shih, S.-R., Pan, M., Li, C., Lue, C.-F., Stellar, V., Li, M.-L., 2009. hnRNP A1 interacts with the 5' untranslated regions of enterovirus 71 and Sindbis virus RNA and is required for viral replication. Journal of virology 83, 6106-6114.
Lin, J.-Y., Li, M.-L., Huang, P.-N., Chien, K.-Y., Horng, J.-T., Shih, S.-R., 2008. Heterogeneous nuclear ribonuclear protein K interacts with the enterovirus 71 5' untranslated region and participates in virus replication. Journal of General Virology 89, 2540-2549.
Lu, J., Yi, L., Zhao, J., Yu, J., Chen, Y., Lin, M.C., Kung, H.-F., He, M.-L., 2012. Enterovirus 71 disrupts interferon signaling by reducing the level of interferon receptor 1 Journal of virology 86, 3767-3776.
Ma, Y., Yu, J., Chan, H.L., Chen, Y.C., Wang, H., Chen, Y., Chan, C.Y., Go, M.Y., Tsai, S.N., Ngai, S.M., To, K.F., Tong, J.H., He, Q.Y., Sung, J.J., Kung, H.F., Cheng, C.H., He, M.L., 2009. Glucose-regulated protein 78 is an intracellular antiviral factor against hepatitis B virus. Molecular & cellular proteomics : MCP 8, 2582-2594.
McMinn, P.C., 2002. An overview of the evolution of enterovirus 71 and its clinical and public health significance. FEMS microbiology reviews 26, 91-107.
Ohlmann, T., Rau, M., Pain, V.M., Morley, S.J., 1996. The C-terminal domain of eukaryotic protein synthesis initiation factor (eIF) 4G is sufficient to support cap-independent translation in the absence of eIF4E. The EMBO journal 15, 1371-1382.
Pérez-Vargas, J., Romero, P., López, S., Arias, C.F., 2006. The peptide-binding and ATPase domains of recombinant hsc70 are required to interact with rotavirus and reduce its infectivity Journal of virology 80, 3322-3331.
Salinas, E., Byrum, S.D., Moreland, L.E., Mackintosh, S.G., Tackett, A.J., Forrest, J.C., 2016. Identification of Viral and Host Proteins That Interact with Murine Gammaherpesvirus 68 Latency-Associated Nuclear Antigen during Lytic Replication: a Role for Hsc70 in Viral Replication. Journal of virology 90, 1397-1413.
Sanz, M.A., Welnowska, E., Redondo, N., Carrasco, L., 2010. Translation driven by picornavirus IRES is hampered from Sindbis virus replicons: rescue by poliovirus 2A protease. Journal of molecular biology 402, 101-117.
Schmidt, N.J., Lennette, E.H., Ho, H.H., 1974. An apparently new enterovirus isolated from patients with disease of the central nervous system. The Journal of infectious diseases 129, 304-309.
Stricher, F., Macri, C., Ruff, M., Muller, S., 2013. HSPA8/HSC70 chaperone protein: structure, function, and chemical targeting Autophagy 9, 1937-1954.
Sztuba-Solinska, J., Diaz, L., Kumar, M.R., Kolb, G., Wiley, M.R., Jozwick, L., Kuhn, J.H., Palacios, G., Radoshitzky, S.R., J. Le Grice, S.F., 2016. A small stem-loop structure of the Ebola virus trailer is essential for replication and interacts with heat-shock protein A8. Nucleic acids research 44, 9831-9846.
Thompson, S.R., Sarnow, P., 2003. Enterovirus 71 contains a type I IRES element that functions when eukaryotic initiation factor eIF4G is cleaved Virology 315, 259-266.
Wang Y, Lee S, Ha Y, Lam W, Chen SR, Dutschman GE, Gullen EA, Grill SP, Cheng Y, Fürstner A, Francis S, Baker DC, Yang X, Lee KH, Cheng YC. Tylophorine Analogs Allosterically Regulates Heat Shock Cognate Protein 70 and Inhibits Hepatitis C Virus Replication. Sci Rep. Aug. 30, 2017;7(1):10037.
Wang, M., Dong, Q., Wang, H., He, Y., Chen, Y., Zhang, H., Wu, R., Chen, X., Zhou, B., He, J., Kung, H.F., Huang, C., Wei, Y., Huang, J.D., Xu, H., He, M.L., 2016. Oblongifolin M, an active compound isolated from a Chinese medical herb Garcinia oblongifolia, potently inhibits enterovirus 71 reproduction through downregulation of ERp57. Oncotarget 7, 8797-8808.
Wang, Y., Zou, G., Xia, A., Wang, X., Cai, J., Gao, Q., Yuan, S., He, G., Zhang, S., Zeng, M., 2015. Enterovirus 71 infection in children with hand, foot, and mouth disease in Shanghai, China: epidemiology, clinical feature and diagnosis. Virology journal 12, 83.
Wang, S.-M., Liu, C.-C., 2014. Update of enterovirus 71 infection: epidemiology, pathogenesis and vaccine. Expert Review of Anti infective Therapy 12, 447-456.

(56) References Cited

OTHER PUBLICATIONS

Wang, Y.-P., Liu, F., He, H.-W., Han, Y.-X., Peng, Z.-G., Li, B.-W., You, X.-F., Song, D.-Q., Li, Z.-R., Yu, L.-Y., 2010. Heat stress cognate 70 host protein as a potential drug target against drug resistance in hepatitis B virus. Antimicrobial agents and chemotherapy 54, 2070-2077.

Watanabe, K., Takizawa, N., Noda, S., Tsukahara, F., Maru, Y., Kobayashi, N., 2008. Hsc70 regulates the nuclear export but not the import of influenza viral RNP: A possible target for the development of anti-influenza virus drugs. Drug Discov Ther 2, 77-84.

Watanabe, K., Fuse, T., Asano, I., Tsukahara, F., Maru, Y., Nagata, K., Kitazato, K., Kobayashi, N., 2006. Identification of Hsc70 as an influenza virus matrix protein (M1) binding factor involved in the virus life cycle. FEBS letters 580, 5785-5790.

Yi, L., Lu, J., Kung, H.F., He, M.L., 2011. The virology and developments toward control of human enterovirus 71. Critical reviews in microbiology 37, 313-327.

Zárate, S., Cuadras, M.A., Espinosa, R., Romero, P., Juarez, K.O., Camacho-Nuez, M., Arias, C.F., López, S., 2003. Interaction of rotaviruses with Hsc70 during cell entry is mediated by VP5 Journal of virology 77, 7254-7260.

Zhang, H., Song, L., Cong, H., Tien, P., 2015. Nuclear protein Sam68 interacts with the enterovirus 71 internal ribosome entry site and positively regulates viral protein translation. Journal of virology 89, 10031-10043.

Zhu, B., Xu, T., Lin, Z., Wang, C., Li, Y., Zhao, M., Hua, L., Xiao, M., Deng, N., 2017. Recombinant heat shock protein 78 enhances enterovirus 71 propagation in Vero cells and is induced in SK-N-SH cells during the infection. Archives of Virology 162, 1649-1660.

Ziegler, E., Borman, A.M., Deliat, F.G., Liebig, H.D., Jugovic, D., Kean, K.M., Skern, T., Kuechler, E., 1995. Picornavirus 2A proteinase-mediated stimulation of internal initiation of translation is dependent on enzymatic activity and the cleavage products of cellular proteins. Virology 213, 549-557.

\* cited by examiner

A

SEQUENCE LISTING

```
<160> NUMBER OF SEQ ID NOS: 12

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uaauucuaag uacauugaga ccagc                                             25

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 2
ccuaaauucg uagcaaauu                    19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcagcccaaa agaacttcac                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atttcagcag cttggagtgc                    20

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgcattgggc gaggtatc                      18

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggactgtag gcacctcgaa                    20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
actccaagct atgtcgcctt t                  21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 8
tggcatcaaa aactgtgttg gt                                              22

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gattccaccc atggcaaatt cca                                             23

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggtgatggg atttccattg atga                                            24

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccgaattcat ggggaaattt gggcaacag                                       29

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcactcgagc tgctccatag cttcttc                                         27
```

METHODS OF TREATMENT OF VIRAL INFECTION AND USES OF ANTI-HSC70 INHIBITORS

SEQUENCE LISTING

The instant application contains a Sequence Listing which has been filed electronically in ASCII format and is hereby incorporated by reference in its entirety. Said ASCII copy, created on Jan. 31, 2019, is named 2958_043_SL.txt and is 2,995 bytes in size.

FIELD OF THE INVENTION

The present invention is concerned with uses of anti-Hsc70 inhibitors and methods of treatment of viral infection.

BACKGROUND OF THE INVENTION

There is a wide range of viral infections which pose different extents of health treats to the humans. For example, hand, foot, and mouth diseases (HFMD) are caused by viral infection, highly infectious, and have become one of the recent health challenges. Although HFMD was first reported in California in 1969, it has become particularly problematic in Asia in the past two decades. The Chinese government has reported more than 3,000 of deaths after the first nationwide outbreak of HFMD in 2008. Obviously, HFMC, caused by EV-A71 infection, has become a serious public health problem.

One way to address different viral infections is to design specific pharmaceutical chemicals which would inhibit proliferation of the respective viruses. This can be effective to some extent from a treatment point of view. However, designing specific effective chemicals for different infectious viruses would take years. The inventors contemplated that the public would benefit tremendously if a treatment regime could more comprehensive in treating different viral infections.

The present invention seeks to address the above issues, or at least to provide alternatives to the public.

SUMMARY OF THE INVENTION

According to a first aspect of the present invention, there is provided a method of treatment of viral infection comprising a step of administering an anti-Hsc70 inhibitor.

According to a second aspect of the present invention, there is provided a use of an anti-Hsc70 inhibitor for treatment of viral infection. The anti-Hsc70 inhibitor may be an interfering RNA. The anti-Hsc70 may be a siRNA. The siRNA may have a sequence of 5'-UAAUUCUAAGUA-CAUUGAGACCAGC-3' (SEQ ID NO: 1).

Preferably, the anti-Hsc70 inhibitor may be a chemical inhibitor. The chemical inhibitor may be Ver-155008.

In an embodiment, the viral infection may be an infection from enteroviruses or RNA viruses.

In one embodiment, the viral infection may be a flaviviral infection.

In specific embodiments, the infection may be selected from the group consisting of Zika virus infection, Hepatitis virus infection, West Nile virus, Dengue virus infection, Tick-borne Encephalitis virus infection, and yellow fever virus.

According to a third aspect of the present invention, there is provided a method for modulating activity of virus in a subject, comprising a step of controlling the level of Hsc70 in the subject. The modulating may be inhibiting the activity of the virus for treatment of viral infection.

Preferably, the method may comprise a step of administering an anti-Hsc70 inhibitor. The anti-Hsc70 inhibitor may be an interfering RNA.

Suitably, the anti-Hsc70 may be siRNA. The siRNA may have a sequence of 5'-UAAUUCUAAGUACAUUGA-GACCAGC-3' (SEQ ID NO: 1).

In an embodiment, the anti-Hsc70 inhibitor may be a chemical inhibitor. The chemical inhibitor may be Ver-155008.

In one embodiment, the viral infection may consist of enteroviral and flaviviral infection.

In specific embodiments, the viral infection may be selected from the group consisting of Zika virus infection, Hepatitis virus infection, West Nile virus, Dengue virus infection, Tick-borne Encephalitis virus infection, and yellow fever virus.

BRIEF DESCRIPTION OF THE DRAWINGS

Some embodiments of the present invention will now be explained, with reference to the accompanied drawings, in which:—

DETAILED DESCRIPTION OF PREFERRED EMBODIMENTS OF THE INVENTION

Figure 1A:
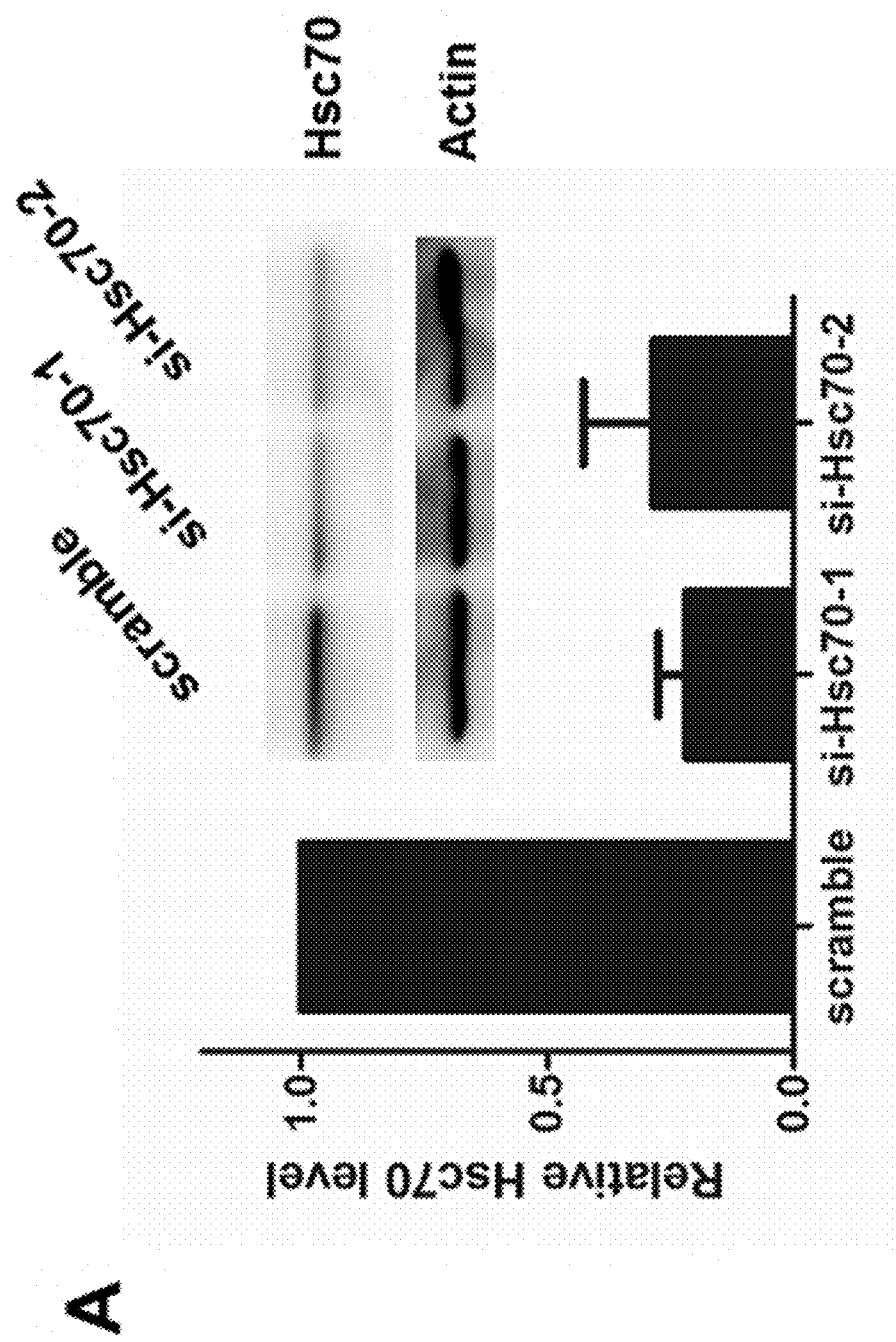
FIGS. 1A to 1E are representations showing Inhibition Hsc70 reduced EV-A71 infection.

Enterovirus A71 (EV-A71) is a small positive-stranded RNA virus with a 7.4 kb genome which can be translated into four structural proteins (VP1-VP4) and seven nonstructural proteins. Infection of EV-A71 would lead to Hand, Foot, and Mouth diseases (HFMD). Although HFMD is generally relatively mild and self-limited in most cases, EV-A71 is highly infectious. In young children, it can still cause severe neurological disorders or even death in extreme cases. Since the first report in California during 1969, large outbreaks of HFMD, which are mainly caused by EV-A71 infection, have repeatedly occurred in Asia-Pacific region in recent years.

The initiation of viral protein translation is driven by the internal ribosome entry site (IRES) in the 5'-UTR in a cap-independent manner. The IRES of EV-A71 is a type I IRES with five stem-loops (domain II-VI) spanning about 500 nucleotides. The translation of enterovirus was promoted by the viral protein 2A ($2A^{pro}$) which was a well-known protease in disturbing host cell translation by cleaving eIF4G. It has been well known that the proteolytic activity of $2A^{pro}$ was necessary for the enhancement of IRES activity. The translation driven by IRES was also regulated by cellular IRES-binding proteins, which are defined as IRES trans-acting factors (ITAFs). The inventors have realized that several ITAFs are to regulate EV71 IRES mediated translation such as upstream element binding protein (FBP) 1-3, hnRNP K and hnRNP A.

Heat shock cognate protein 70 (Hsc70, also called HSPA8), a member of Hsp70 family, is a molecular chaperone that carries out pivotal functions in many cellular processes. An important role of Hsc70 is to regulate the clathrin-mediated endocytosis, the process participates in the entry of Rotavirus and Japanese encephalitis virus. It has been reported that Hsc70 is an important host protein regulating viral RNA replication such as hepatitis C virus (HCV), influenza (Watanabe et al., 2006). Hsc70 directly binds with HCV viral protein NS5A and participates in the virion assembly. Hsc70 also contributes to the trafficking of Coxsackievirus B3 (CVB3) by acting as a chaperone. The role of HSC70 in EV-A71 infection is unknown.

During the course leading the present invention, the inventors have shown that Hsc70 plays an important role in EV-A71 infection through enhancing IRES activity; and HSC70 inhibitor efficiently inhibits viral replication. Accordingly, there is provided methods of, for example, a first level broad treatment of viral infections by way of anti-Hsc70 inhibitors. The following are details of experiments showing the workability of anti-Hsc70 inhibitors 1. Materials and Methods 1.1 Viruses and Cells Human rhabdomyosarcoma (RD) cells were purchased from ATCC (CCL-136). The Dulbecco's modified Eagle's medium (DMEM) with 10% fetal bovine serum (FBS) were used for cell culture, supplemented with 100 U/ml penicillin and 100 μg/ml streptomycin Propagation of EV-A71 (SHZH98 strain, accession number AF302996) was the same as previous report. The viral titer was measured by $TCID_{50}$ assays.

1.2 RNA Interference

The small interfering RNA (siRNA) targeting human Hsc70 (NM_006597) (si-Hsc70-1: 5'-UAAUUCUAAGUA-CAUUGAGACCAGC-3' (SEQ ID NO: 1); si-Hsc70-2: 5'-CCUAAAUUCGUAGCAAAUU-3' (SEQ ID NO: 2)) were synthesized from Genepharma (Shanghai, China). RD cells were transfected with the siRNAs at a final concentration of 75 nM for 48 hours by HiPerfect (Qiagen) as our previous reports. A scrambled siRNA not targetting human genome was used as control and transfected at the same concentration. Then the total RNA or protein was collected to test the knockdown efficiency by qPCR or Western blot assays.

1.3 Plasmids Construction

Human Hsc70 (Accession NM_006597) was purchased from Addgene (Cat. No. 19541). The EV-A71 report plasmid pIRES was constructed as previously described. In detail, the EV-A71 reportor plasmid pIRES was constructed as follows: *Renilla* Luciferase gene (RLuc) was inserted into pcDNA4/HisMax B between BamHI and EcoRV sites; EV-A71 IRES was amplified from EV-A71 virus strain (SHZH98). Firefly Luciferase gene (FLuc) was amplified by using primer which has overlap sequence with the C-terminal of EV-A71 IRES. Finally, the construct IRES-FLuc were then amplified by using overlap PCR, and inserted into the downstream of the *Renilla* Luciferase gene between EcoRV and XbarI sites. The control plasmid pRF was constructed in similar way except containing EV-A71 IRES in the upstream of FLuc gene. The FLuc gene was amplified and then inserted into the downstream of the *Renilla* Luciferase gene between EcoRV and XbarI sites. Plasmid pET28a-$2A^{pro}$ was amplified by PCR from cDNA clone of EV-A71 and inserted into pET28a. The primers for $2A^{pro}$ were listed in Table 1. All primers used in plasmids construction are available upon request.

1.4 Luciferase Assays

HEK 293T cells were seeded into a 24-well plate and incubated at 37° C. overnight and then transfected with Hsc70 expression plasmid (pHsc70) or siRNA. After 24 hours of transfection, cells were then transfected with pIRES or pRF plasmids for another 24 hours and was extracted by passive buffer (Promega, USA) on the ice. To investigate the effects of Hsc70 and $2A^{pro}$ on IRES, 50 ng of pIRES, 125 ng of 2A-expressing plasmid and 500 ng of pHsc70 was co-transfected into HEK293 cells. The activity of RLuc and FLuc were assessed by bioluminometer using a dual-luciferase reporter assay (Promega) according to the manufacturer.

1.5 Expression and Purification of Recombinant Proteins pET28a-$2A^{pro}$ was transformed into Lemo21 competent *E. coli*. (NEB, USA). Protein expression was induced by 30 uM isopropyl-3-D-thiogalactopyranoside at 16° C. overnight. The recombinant His-tagged $2A^{pro}$ was purified using Ni-NTA agarose (Qiagen, Germany) according to the manufacturer. The purity of $2A^{pro}$ was verified by 15% sodium dodecyl sulfate-polyacrylamide gel ((SDS-PAGE).

1.6 RNA Immunoprecipitation and RNA Pull-Down

RD cells were infected with EV-A71 at an MOI of 10 for 6 hours and lysed with a lysis buffer (50 mM Tris-HCl, pH7.4, 150 mM NaCl, 1 mM EDTA, and 0.5% TritonX-100) with protease inhibitor cocktail (Roche, USA) and RNasin (Promega, USA). RNA immunoprecipitation (RIP) was performed by using the Hsc70 antibody and normal IgG as a negative control to co-precipitate the RNA at 4° C. for 1 hour. The binding RNAs were assessed by qRT-PCR. The PCR product was subjected to an agarose gel. For the RNA pull-down assay, the biotin labeled 5'-UTR (1-745 nt) or full-length viral RNA was transcribed with the Biotin RNA Labeling Mix (Roche, USA) and T7 RNA polymerase (Roche, USA) in vitro and then incubated with the cell lysate. The RNA-protein complex was pulled down by the streptavidin beads following an immunoblotting using Hsc70 or hnRNP A antibodies.

1.7 Protein Pull-Down

The protein pull-down assay was performed as previously described. In brief, the recombinant His-$2A^{pro}$ was immobilized onto Ni-NTA resin and then incubated with 293T cell lysates at 4° C. for one hour. After wash, the pull-down complex was subjected to immunoblot with an anti-Hsc70 or hnRNP A antibody.

1.8 In Vitro Protease Cleavage Assay

Cells were extracted by using a cleavage buffer (0.1% Triton X-100, 100 mM KCl, 50 mM NaCl, 80 mM Tris-HCl, pH 8.0, 1 mM CaCl2), 0.1 mM EDTA and 1 mM DTT) without protease inhibitors as reported. After centrifuged at 20,000 g for 20 min at 4° C., the supernatant was collected. Fifteen μg of cell extract was incubated with 2 ug of $2A^{pro}$ in the cleavage buffer at 30° C. for 4 h. The reaction was stopped by SDS loading buffer. The cleavage products were resolved by SDS-PAGE and analyzed by immunoblotting using anti-Hsc70 and anti-eIF4G.

1.9 Western Blotting Analysis

Total protein was extracted from cell lysis in RIPA buffer with protease inhibitor and phosphatase Inhibitor (Roche). A total of 10-30 μg protein was loaded for SDS-PAGE and transferred onto PVDF membranes. Membranes were blocked with 5% non-fat milk in Tris-buffered saline buffer with 0.1% Tween-20 (TBST) for 1 hour at room temperature and incubated with primary antibodies overnight at 4° C. After washing with TBST three times, the membranes were incubated with the corresponding horseradish peroxidase (HRP)-conjugated secondary antibodies for 1 hour at room temperature. The Hsc70 protein level was detected using an Hsc70-specific antibody (sc-13132, Santa Cruz Biotechnology, USA). The band density was quantified using Quantity One software (Bio-Rad). GADPH served as loading control. The western blotting was carried out in three times for confirmation of results.

1.10 RNA Extraction and qRT-PCR Analyses

Total RNA was extracted from cell lysis using TRIzol reagent (Ambion, Life Technologies). Quantitative Real-time PCR (qRT-PCR) was performed using SYBR Green Mix (Life Technologies) on applied Biosystems StepOne real-time PCR system. The comparative ΔΔCt method was used to calculate the relative expression of microRNA or mRNA normalized to β-actin mRNA. The primer sequences are listed in Table 1.

1.11 Cytopathic Effect (CPE) Assay

CPE assay was used to test the antiviral effect of Ver-155008. Ver-155008 was from Selleckchem (Cat. No. S7751). RD cells were seed in 96-well plate at 37° C. overnight, was then treated with indicated concentration of Ver-155008. After 2 hours of preincubation of Ver-155008, cells were infected with EV-A71 at cells were infected with EV-A71 at MOI of 0.01. CPE was monitored and recorded from time to time under a phase-contrast microscope. The concentration required to reduce the EV-A71-induced CPE by 50% (IC50) was determined by using the nonlinear regression analysis of SPSS 17.0. Data were shown as mean values with standard deviations from three independent assays. Selectivity index (SI) is calculated by the ratio of CC50 to IC50.

1.12 Cell Viability Assay

RD cells were seeded in 96-well plates (5,000 cells/well) and treated with serial dilution of Ver-155008 for 24 hours for cell viability assay. Ten μL of MTT was added to cultured cells in 100 μl culture medium and incubated at 37° C. for 4 h. Subsequently 100 μl of Dimethyl Sulfoxide were added. The optical density was measured at a wavelength of 570 nm. The cell viability assay was carried out in triplicates by three independent experiments as previously described.

1.13 Statistical Analysis

Results are expressed as the mean±standard deviation (SD). All statistical analyses were carried out with SPSS 14.0 software (SPSS Inc.). Two-tailed Student's t test was applied for two-group comparison. A P value less than 0.05 was defined as significant.

2. Results

2.1 Knockdown of Hsc70 Reduced EV-A71 Replication

To reveal the role of Hsc70 in EV-A71 infection, we first explored the effect of Hsc70 on EV-A71 infection using siRNA knockdown approaches.

Figure 1B:
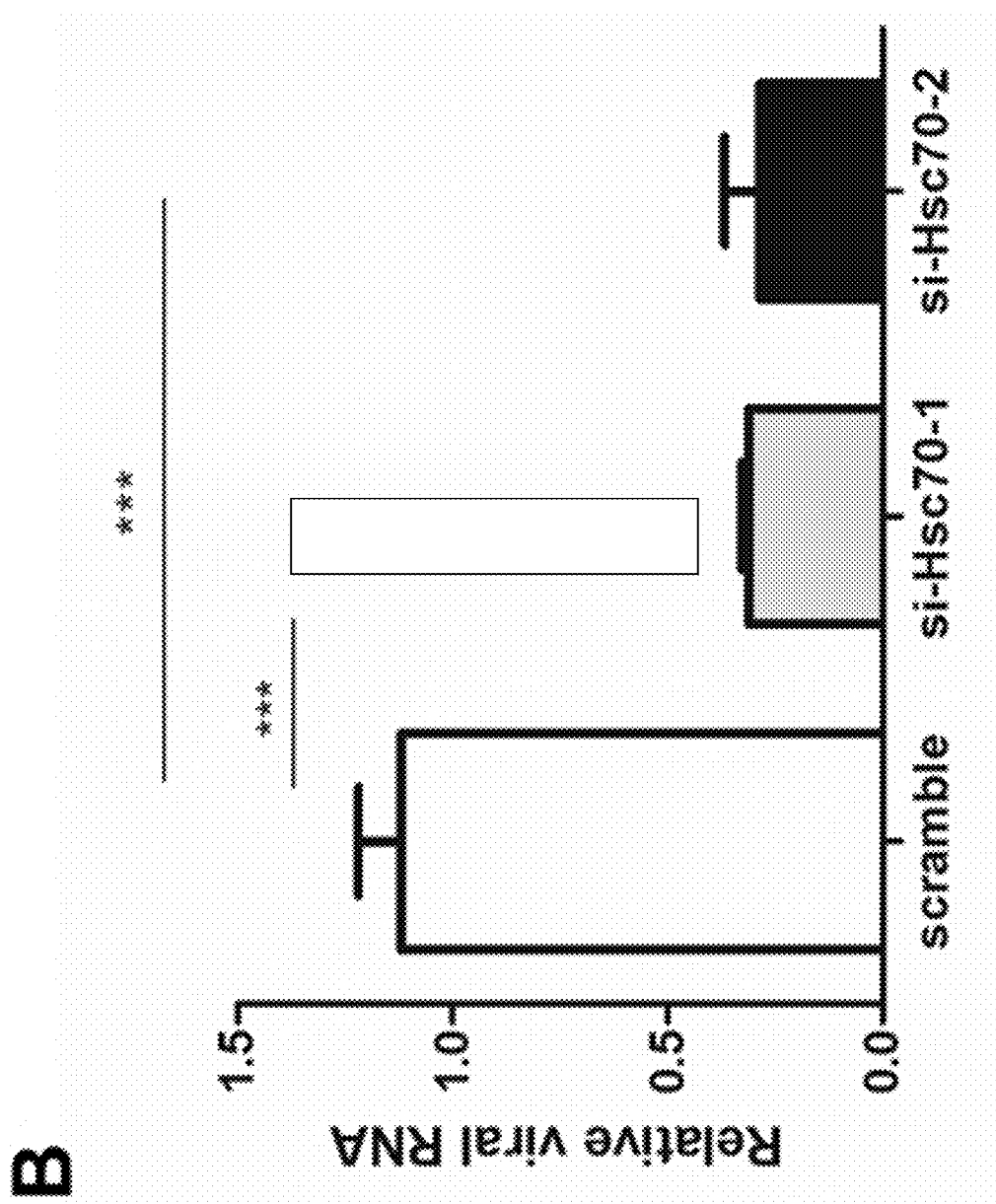
Figure 1C:
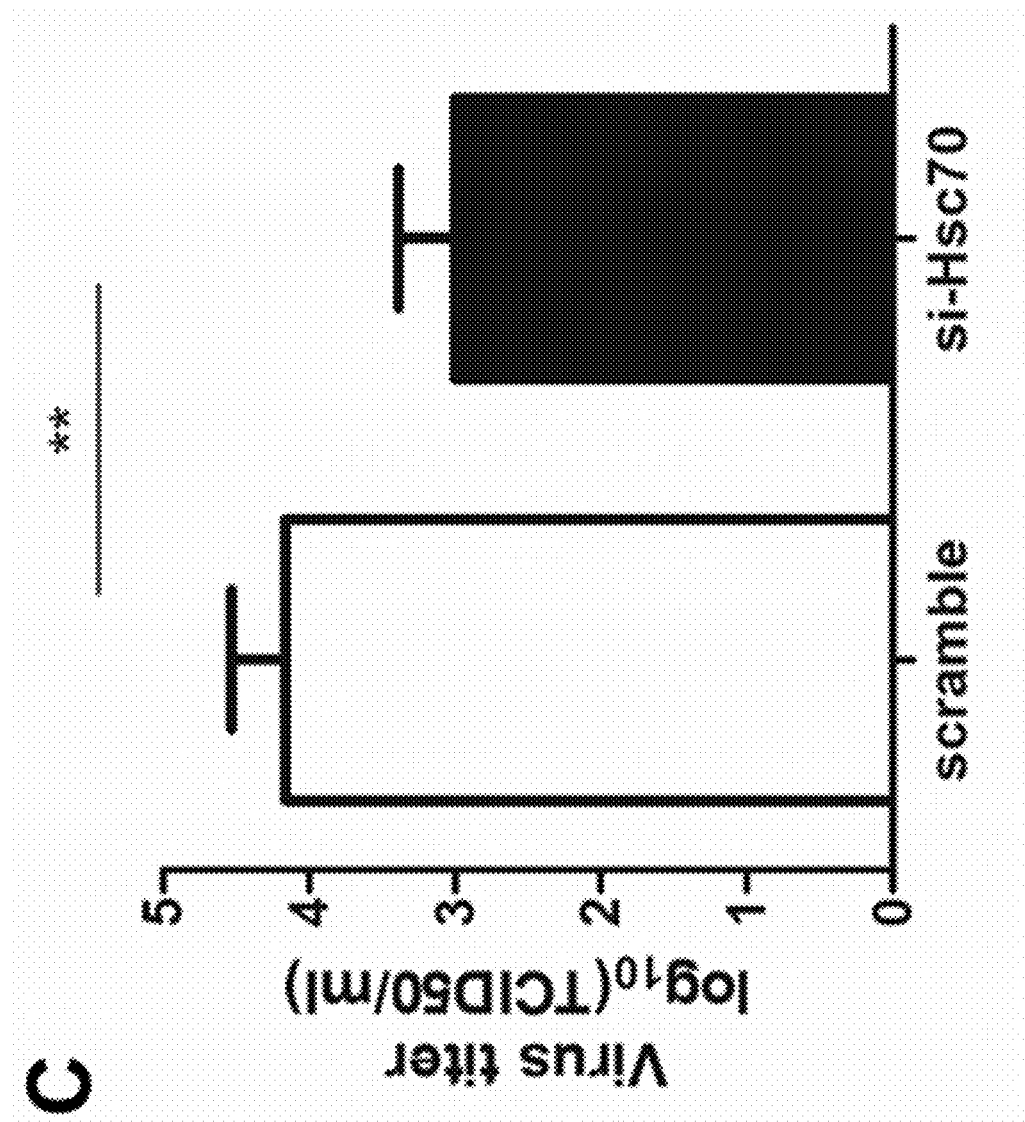
Figure 1D:
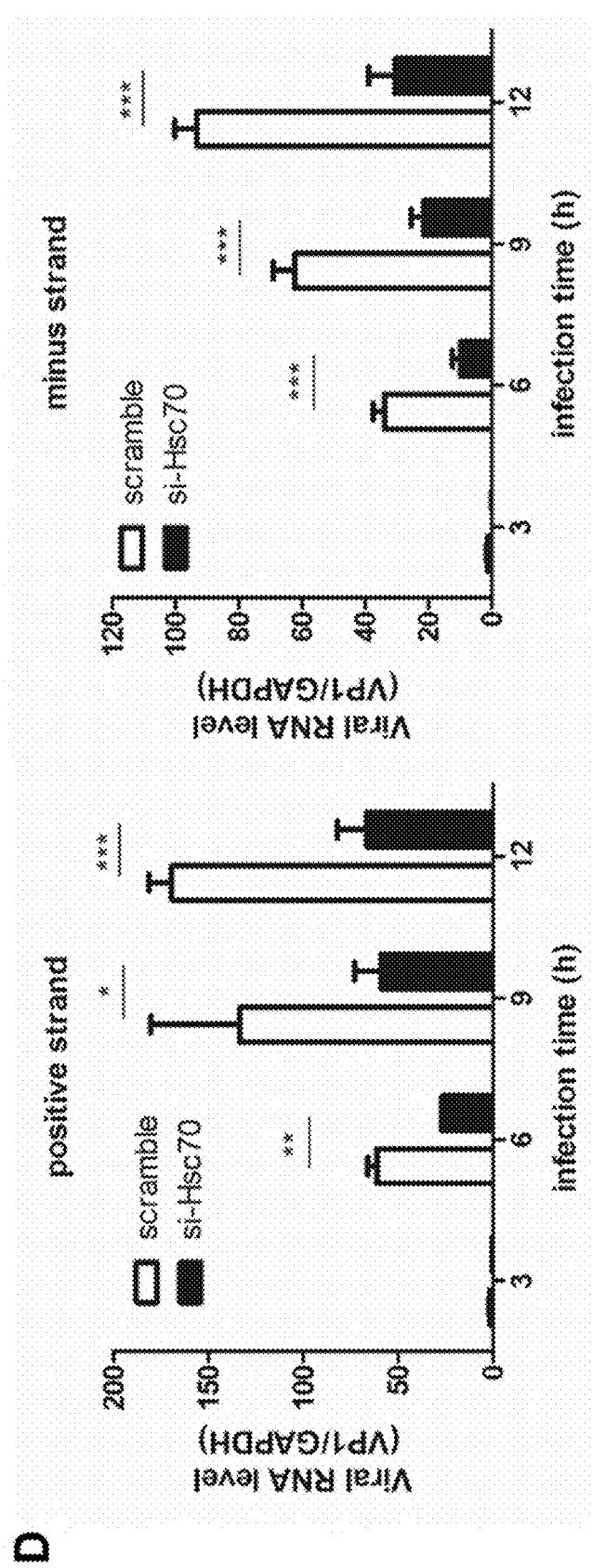
Figure 1E:
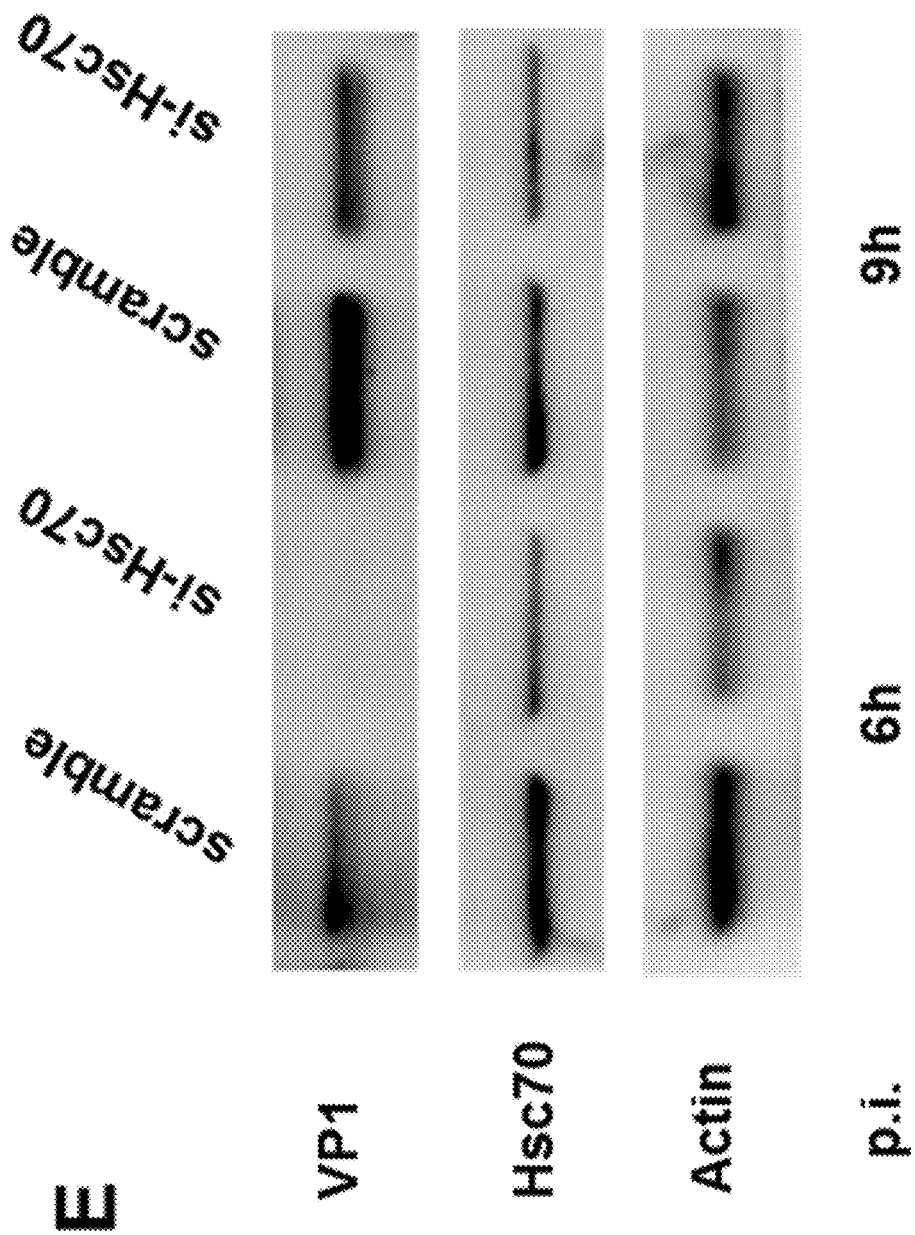

FIG. 1A shows that RD cells were transfected with two Hsc70 specific siRNAs or the scrambled control for forty-eight hours. The mRNA level of Hsc70 was detected by qRT-PCR and the protein level was detected by western blotting. FIG. 1B shows that after forty-eight hours' transfection, RD cells were infected with EV-A71 for 9 hours. The extracellular virus levels were detected by qRT-PCR. FIG. 1C shows that after forty-eight hours' transfection, RD cells were infected with EV-A71 for 9 hours. The viral titer in the supernatant was determined by TCID50 assay. FIG. 1D shows that after forty-eight hours' transfection with siHsc70 or scrambled control, RD cells were infected with EV7 at an MOI of 10 for indicated time. qRT-PCR analysis of EV-A71 minus strand RNA level (right panel) and positive strand (left panel). FIG. 1E shows a western blot of viral protein VP1 (n=3; ***, p<0.001).

Referring to FIG. 1A, knockdown of Hsc70 by specific siRNAs (si-Hsc70-1 and si-Hsc70-2) largely decreased both mRNA and protein levels more than 70%. RD cells were transfected with scrambled or si-Hsc70 for 48 hours following a mock or EV-A71 infection at multiple of infection (MOI) of 10. Nine hours post infection (p.i.), it was found that the virus yield was obviously decreased in the supernatants both from siRNAs treated samples as compared to the scrambled control. Please see FIG. 1B for comparison. With a higher knockdown efficiency and inhibitory effects on virus yield, si-Hsc70-1 (referred to as si-Hsc70 thereafter) was chosen for further studies. We then titrated the viral titers in the culture media. The virus titer decreased more than 10 times (>1 $\log_{10}$) in siRNA treated group as compared with the scramble siRNA control group. Please see FIG. 1C. Then we measured the intracellular viral RNA and protein levels by qRT-PCR and western blot assays at 3, 6, 9, and 12 hours post infection. Compared with the scrambled control, both the cellular viral replication intermediate (viral negative RNA strand, FIG. 1D right panel) and viral genomic RNA (positive strand, FIG. 1D left panel) levels were obviously reduced by si-Hsc70. Both the positive and negative strand viral RNA levels were decreased by about 86% at 3 hours p.i. and about 70% at 6 or 9 hours p.i., respectively. The inhibitory effect of si-Hsc70 was still significant at 12 hours p.i ($p<0.001$). These results were further confirmed by detecting the viral protein levels. Compared to the control cells, EV-A71 viral protein VP1 significantly decreased in the cells with Hsc70 knockdown. Please see FIG. 1E. These data indicated that Hsc70 played an important role in facilitating EV-A71 replication.

2.2 Ectopic Expression of Hsc70 Promoted EV-A71 Infection

To further confirm the effect of Hsc70 on EV-A71 infection, further experiments were conducted.

Figure 2A:
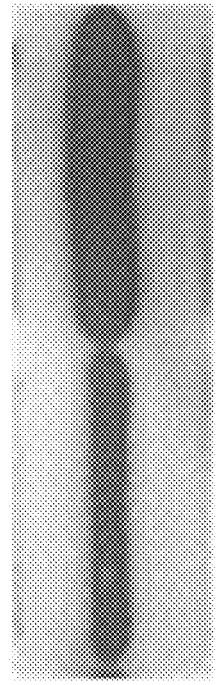
FIGS. 2A to 2E are graphs showing promotion of EV-A71 infection by Hsc70 overexpression.
Figure 2A:
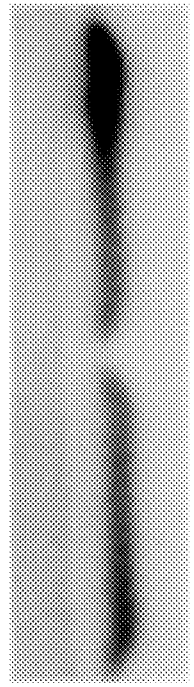
Figure 2B:
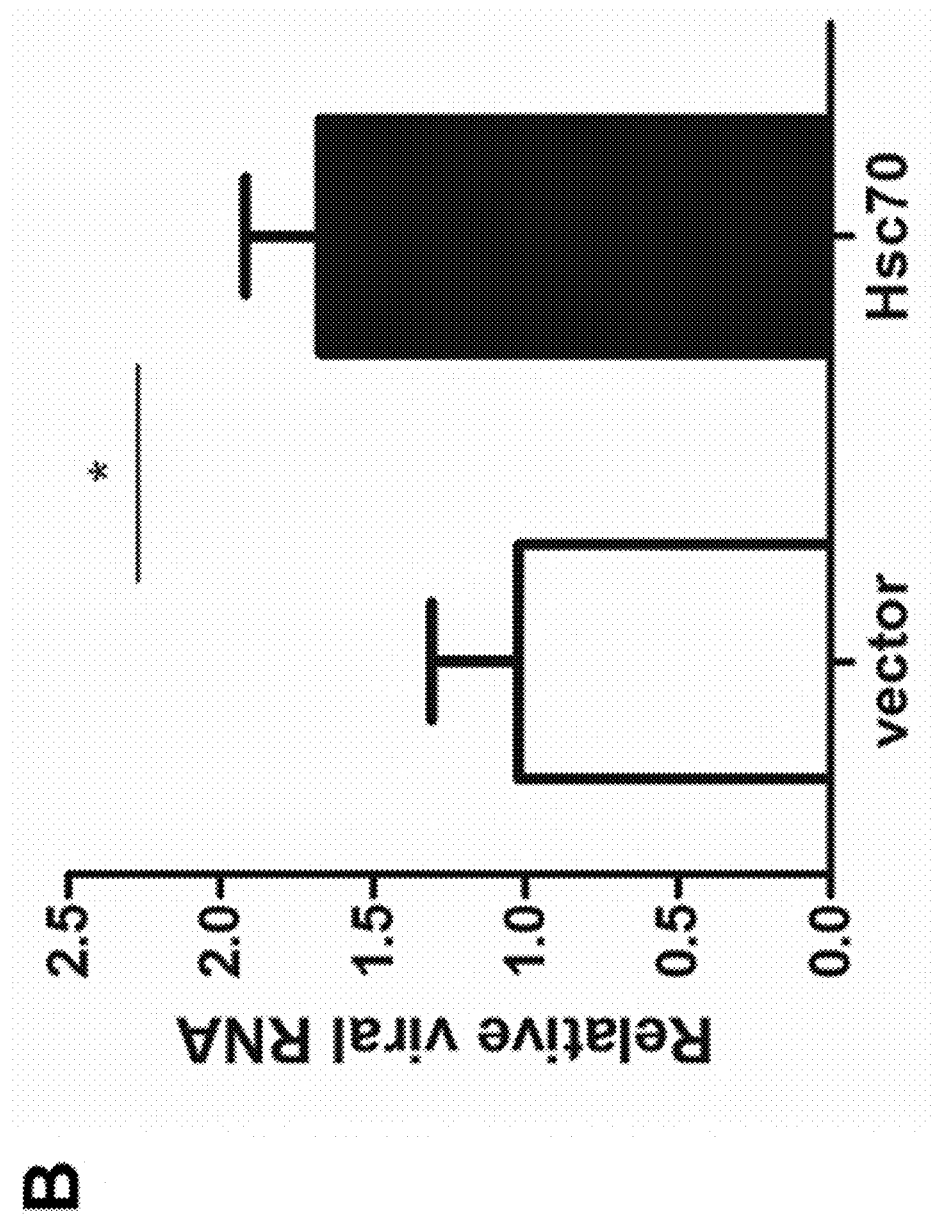
Figure 2C:
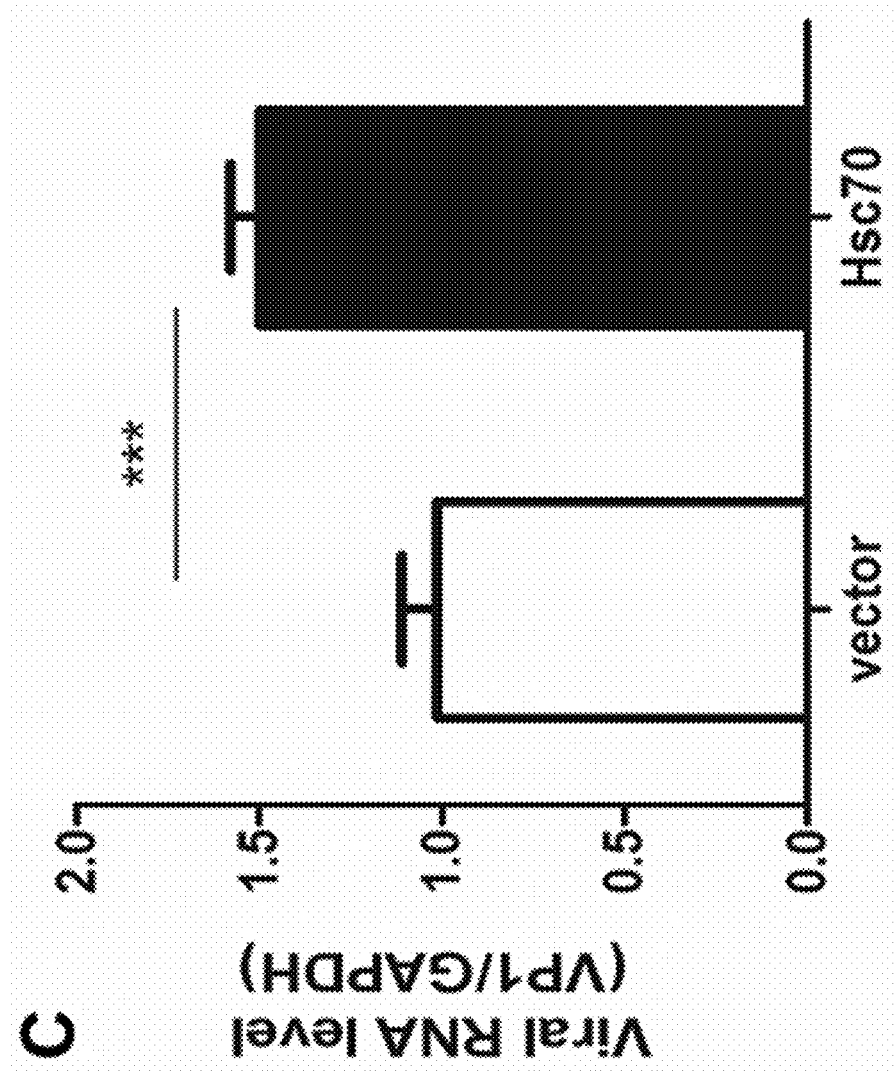
Figure 2D:
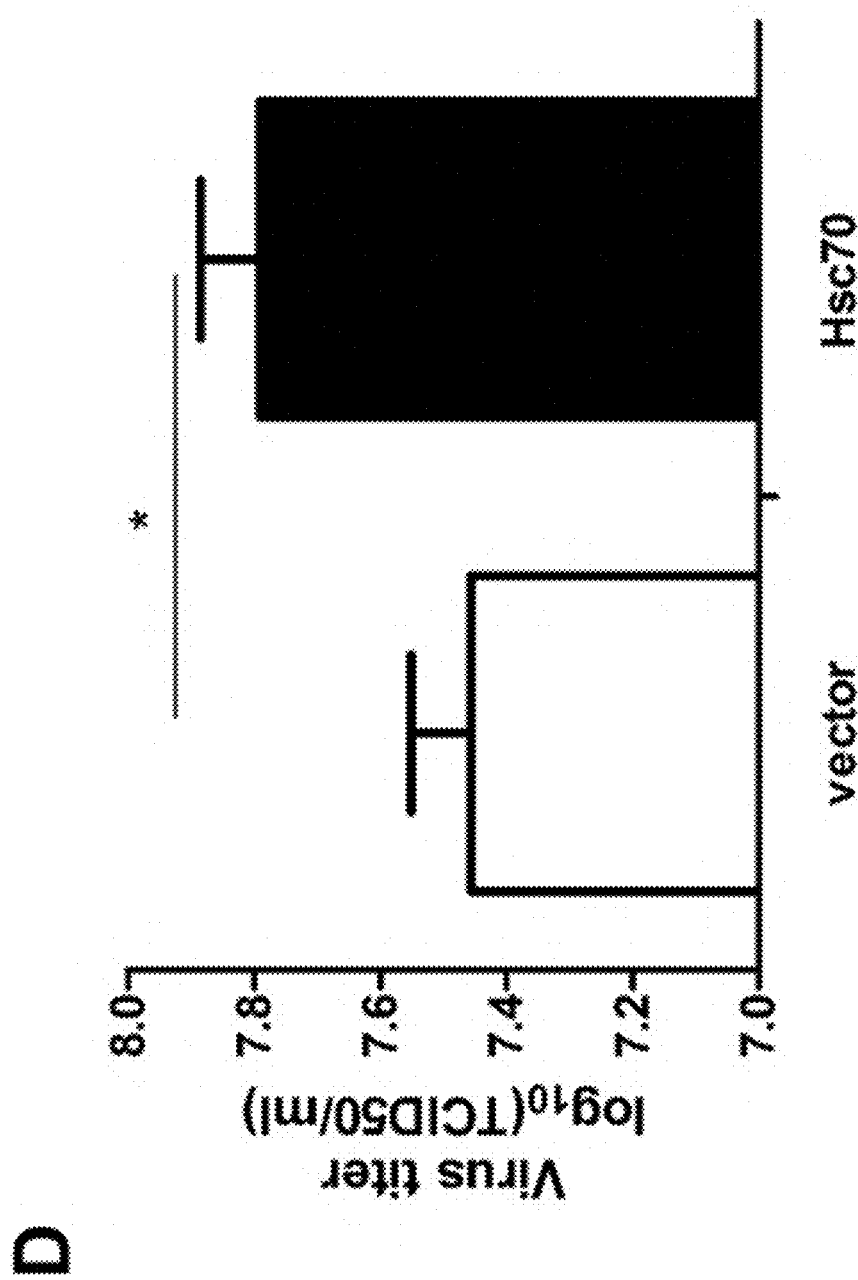
Figure 2E:
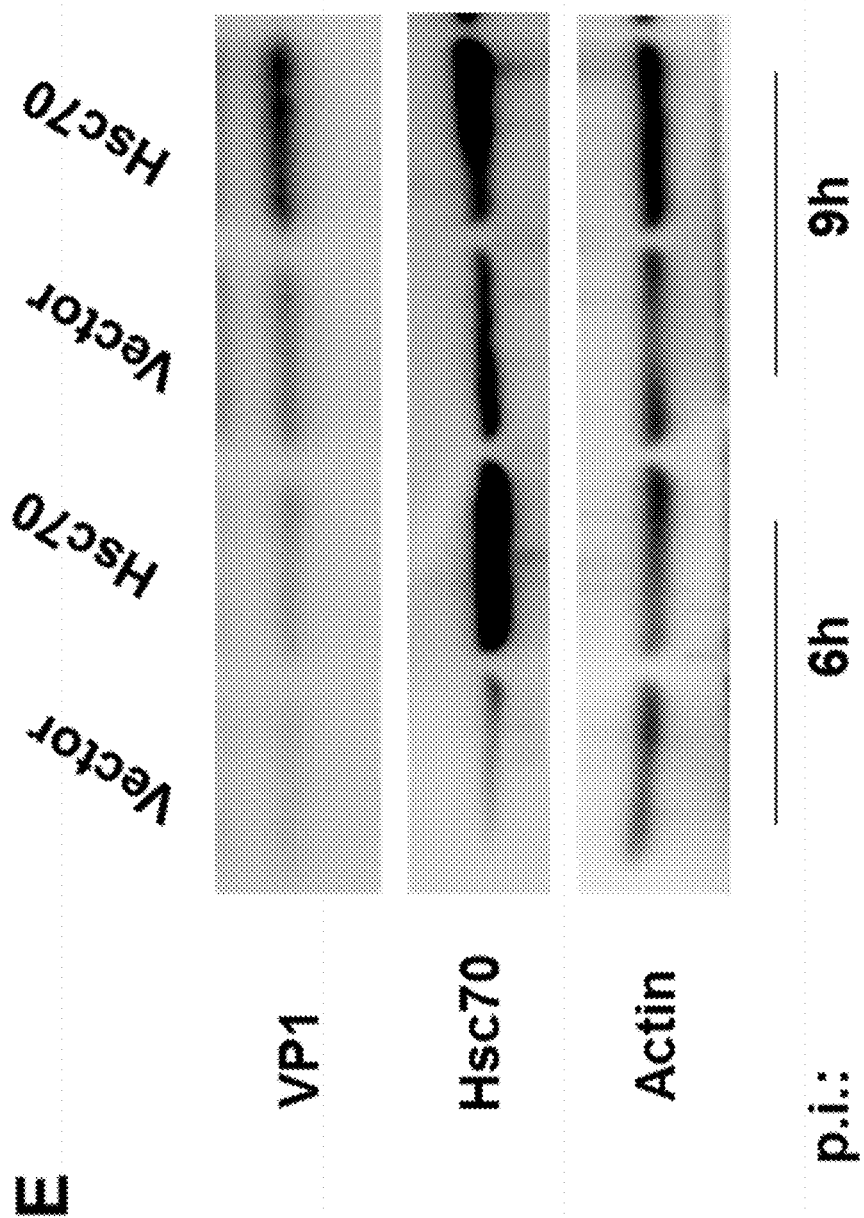

FIGS. 2A to 2E are experiments concerning RD cells transfected with Hsc70 expression plasmid for forty-eight hours. After forty-eight hours' transfection, RD cells were infected with EV-A71 at an MOI of 5 for 9 hours. FIG. 2A shows Hsc70 expression level detected by western blot assays; FIG. 2B shows the extracellular viral RNA levels and FIG. 2C shows the intracellular viral RNA levels examined by qRT-PCR. In FIG. 2D, the viral titer in the supernatant was determined by TCID50 assay. In FIG. 2E, western blotting was performed to detect the protein level of VP1. (n=3; ***, p<0.001)

An expressing plasmid (pHsc70) was transfected and successfully evaluated Hsc70 protein level into RD cells. Please see FIG. 2A. Forty-eight hours p.i., the cells were infected with EV-A71 for 9 hours at an MOI of 5. In agreement with the results from Hsc70 knockdown cells, both the Intra- and extracellular viral RNA levels were significantly higher in the cells with ectopic expressed Hsc70 than that in the control cells. Please see FIG. 2B and FIG. 2C. The virus titers also increased after overexpression of Hsc70 in the supernatants. Please see FIG. 2D. The viral protein VP1 also significantly increased in the cells with ectopic expression of Hsc70 at 6 and 9 hours p.i, respectively. Please see FIG. 2E). Again, this data further confirmed that Hsc70 promoted EV-A71 infection.

2.3 Up-Regulation of IRES Activity by Hsc70

It is known that the viral protein translation was driven in an-IRES dependent way. To however reveal the mechanism of Hsc70 to facilitate EV-A71 infection, its potential effects on IRES activities were examined. A dual reporter system were used in this study.

Figure 3A:
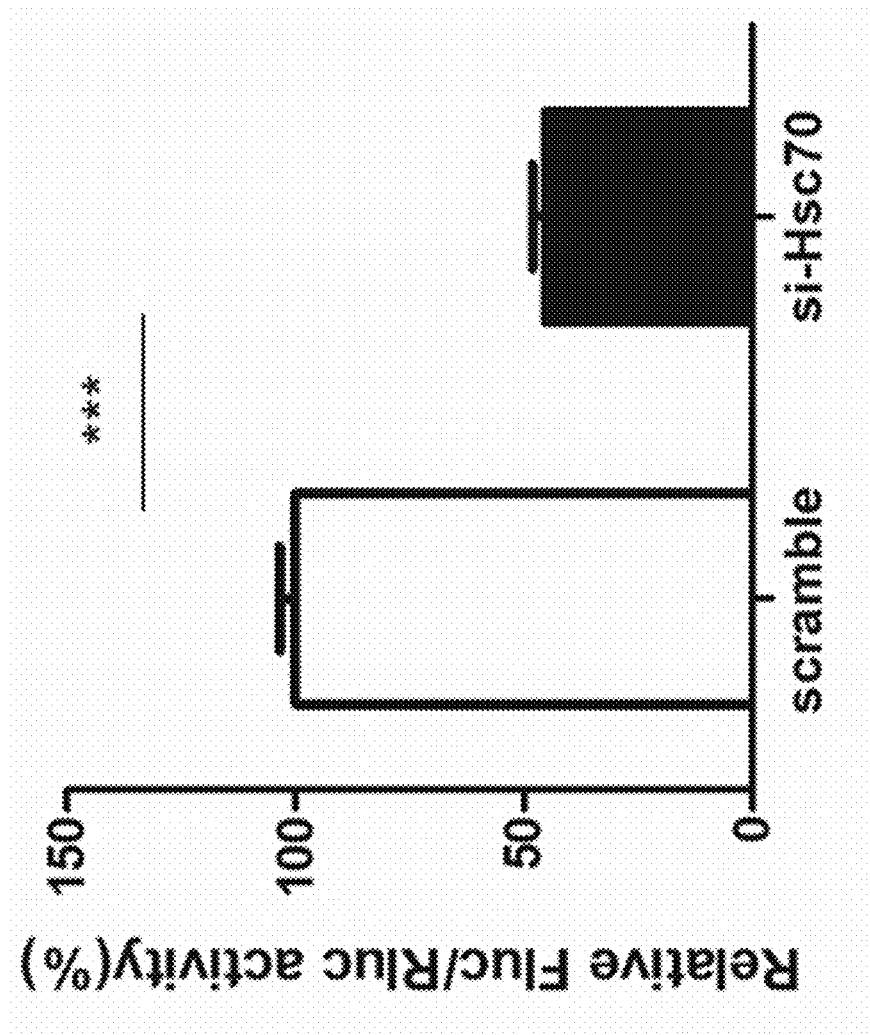
FIGS. 3A to 3D are representation showing promotion of IRES activity by Hsc70.
Figure 3B:
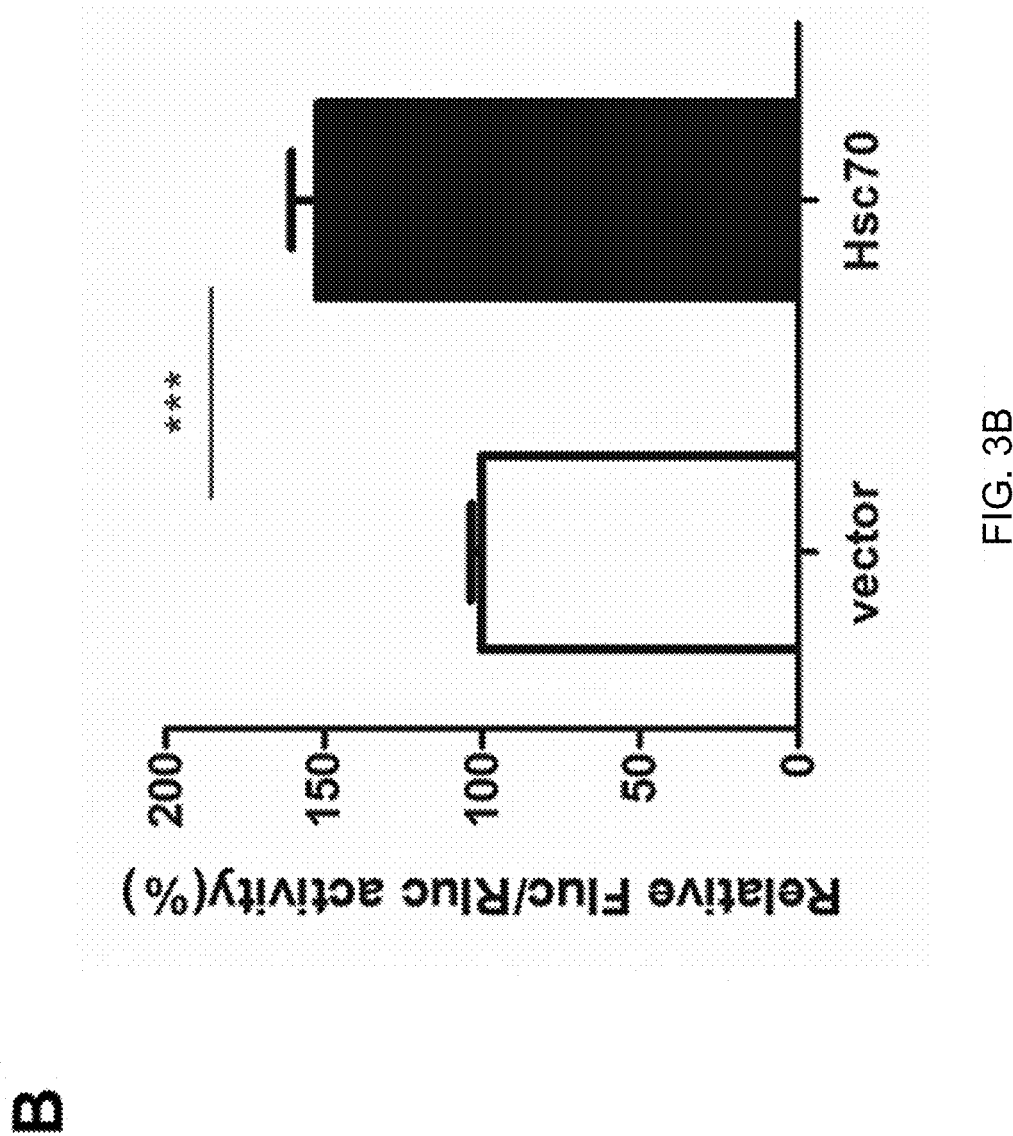
Figure 3C:
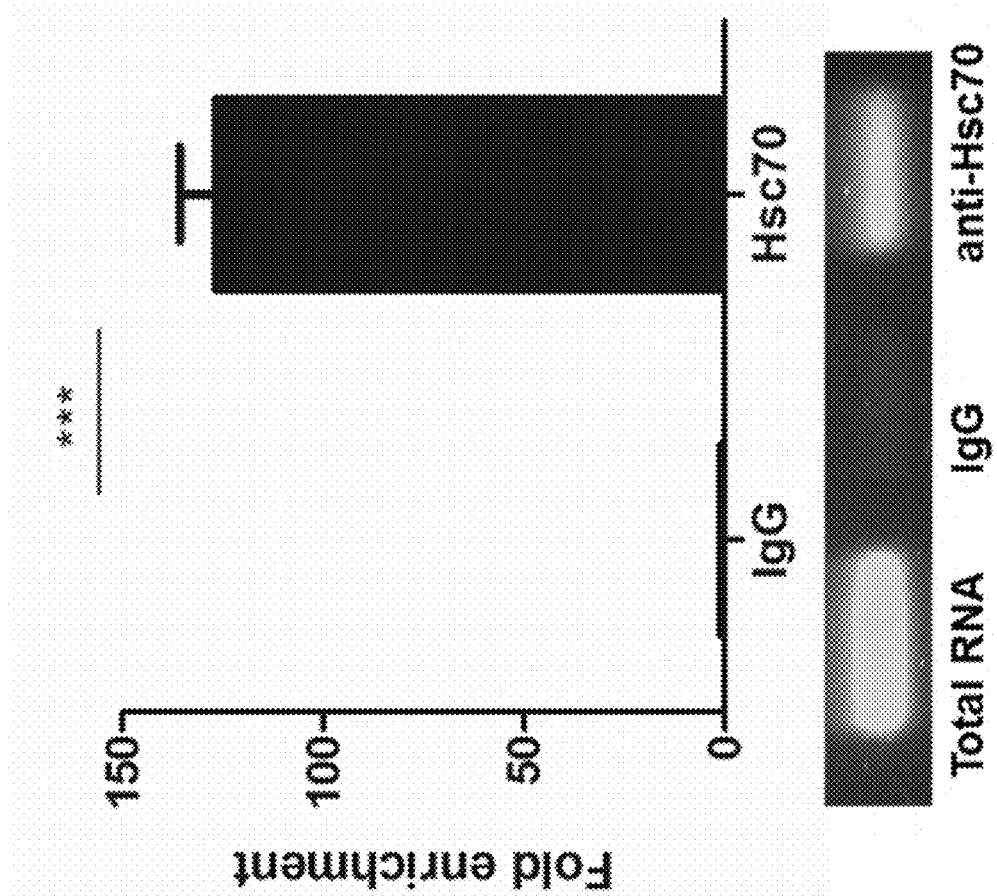
Figure 3D:
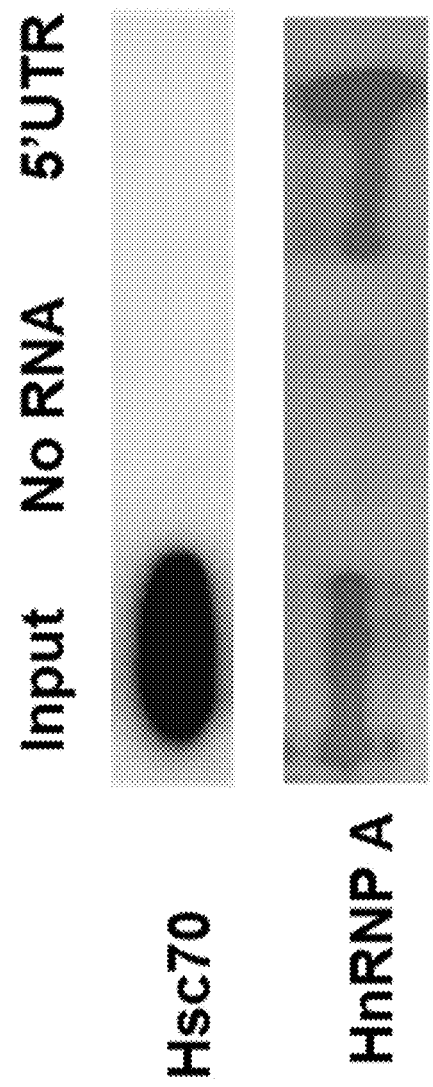

FIG. 3A is concerned with 293T cells were co-transfected with si-Hsc70 and IRES reporter plasmid for forty-eight hours. The IRES activity of EV-A71 at forty-eight hours post-transfection. FIG. 3B is concerned with 293T cells were co-transfected with Hsc70 overexpression and IRES reporter plasmid for forty-eight hours. The IRES activity of EV-A71 at forty-eight hours post-transfection. FIG. 3C is concerned with the biotinylated RNA of 5'-UTR and non-biotinylated RNA incubated with RD cell lysate and then pulled down by the streptavidin beads. Proteins which interact with the RNAs were detected by immunoblotting with specific antibody. FIG. 3D RD cells were infected with EV-A71 and the cell lysate was collected at 6 h p. i. anti-Hsc70 antibody was used in the immunoprecipitation assay. Following washing, the RNA was extracted and subjected to the RT-PCR using EV71 5'UTR-specific primers. (n=3; ***, p<0.001)

It was found that IRES activity largely decreased in Hsc70-depleted cells (please see FIG. 3A), while significantly up-regulated by ectopic expression of Hsc70 (please see FIG. 3B). This data suggested that Hsc70 promoted EV-A71 infection at least partially through regulating IRES activities.

In order ascertain how Hsc70 regulates IRES activity, experiments were then conducted to examine the binding capabilities of Hsc70 to viral RNA by using an immuno-precipitation assay. RD cells were infected with EV-A71 and the cell lysate was collected at 6 hours post infection. An anti-Hsc70 antibody was used to immunoprecipitate the binding RNA and the normal IgG was used as negative control. Following washing, the binding RNA was extracted and subjected to the RT-PCR using EV-A71 5'UTR-specific primers. As shown in FIG. 3C, Hsc70 was able to interact with EV-A71 viral RNA. To reveal whether Hsc70 works as an ITAF through interaction with IRES region, we assessed the association between Hsc70 and 5'-UTR by using an RNA pull-down assay. The biotinylated RNA probe of 5'-UTR (1-745 nt) was incubated with the cell lysate, then the RNA-protein complex was pulled down by streptavidin beads and followed by an immunoblotting using Hsc70 antibody. The hnRNP A, a reported binding protein to 5'-UTR of EV-A71, was used as a positive control; and the nonbiotinylated RNA was used as a negative control. To our surprise, Hsc70 could not directly bind to 5'-UTR of EV-A71. Please see FIG. 3D. Taken together, these results revealed that Hsc70 regulated the IRES activity independent of the association with 5'-UTR of EV-A71.

2.4 Hsc70 Regulate IRES Activity Through Interacting with 2A Protease

The above results indicates that Hsc70 regulated the IRES-driven viral protein translation without a direct binding to EV-A71 IRES. To further ascertain how Hsc70 up-regulates IRES activities, experiments were conducted to check the interaction of Hsc70 and 2A protease ($2A^{pro}$) which had been reported as a positive regulator of IRES activity. It was further examined on whether Hsc70 could affect $2A^{pro}$-mediated IRES activity.

Figure 4A:
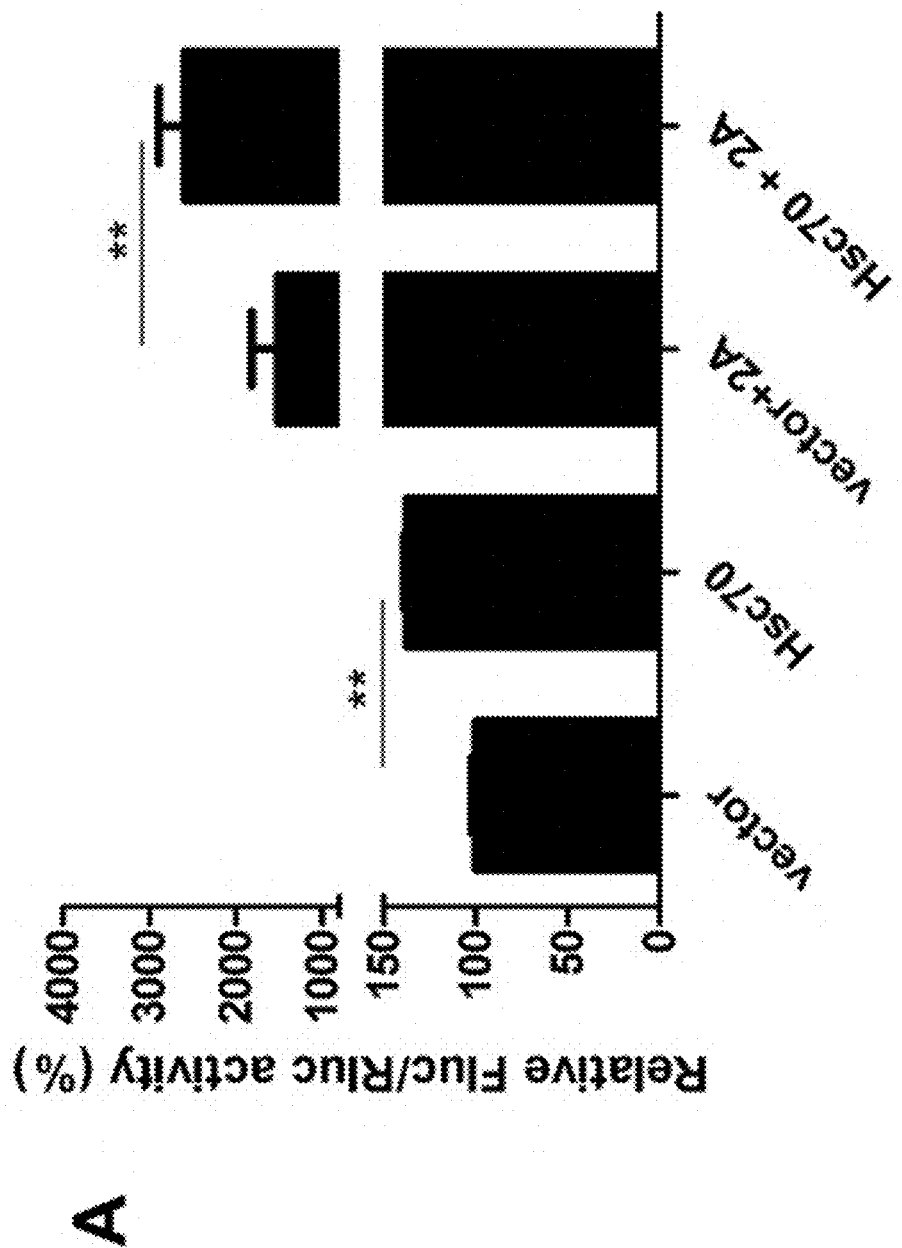
FIGS. 4A to 4D are representations showing Hsc70 regulating IRES activity through interacting with 2A protease.
Figure 4B:
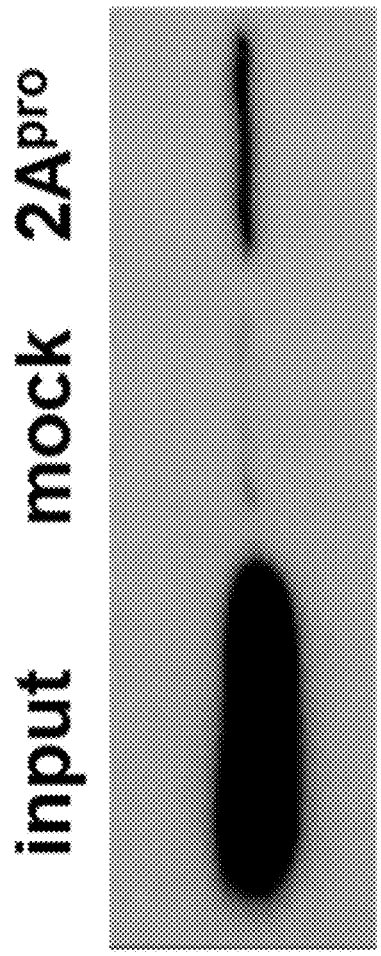
Figure 4C:
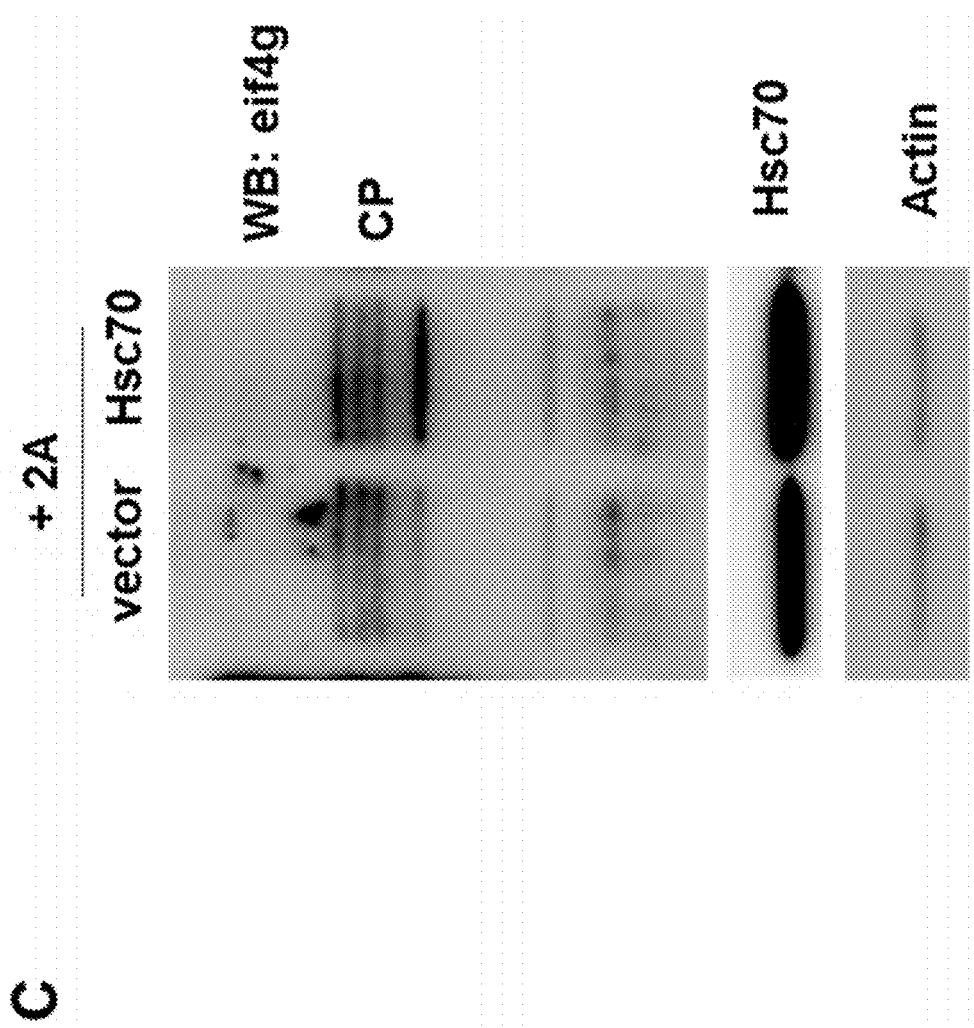
Figure 4D:
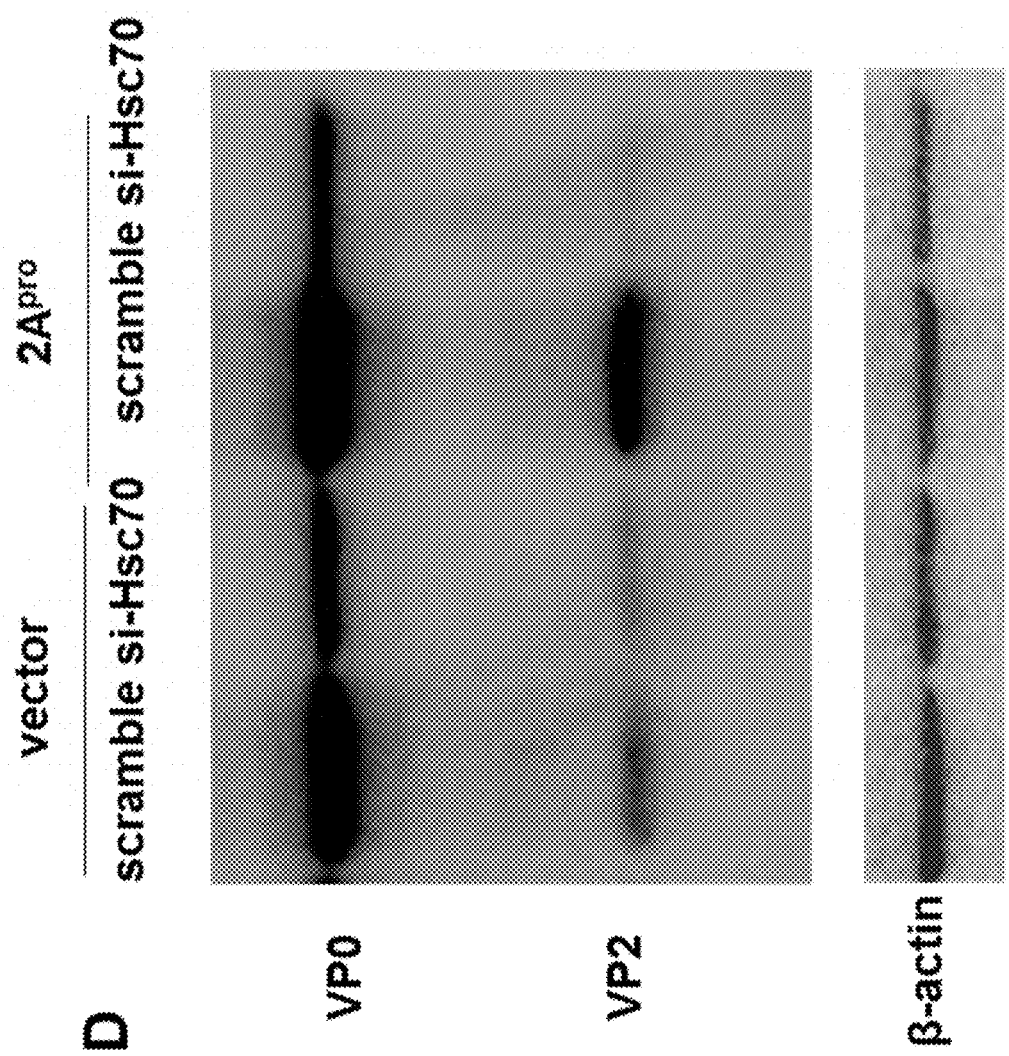

In FIG. 4A, HEK 293T cells were co-transfected with pHsc70, pIRES reporter plasmid and $2A^{pro}$-expressing plasmid or empty vector for forty-eight hours, then the reporter activity was measured. In FIG. 4B, HEK 293T cell extract was incubated with the His-tagged $2A^{pro}$, pulled down and then analyzed by western blotting. In FIG. 4C, HEK 293T cells with or without ectopically expressed Hsc70 were extracted and then cleaved by recombinant $2A^{pro}$ in vitro at 30° C. for 4 hours. The cleavage products were assessed by immunoblotting. In FIG. 4D, HEK 293T cells were transfected with si-Hsc70 or scrambled siRNA for 24 hours and then transfected with the $2A^{pro}$ expression plasmid or empty vector for another twenty-four hours. Cell was infected with EV-A71 at an MOI of 5 for 9 hours. The viral protein production was detected by western blotting by using VP0/2 antibody (n=3).

As shown in FIG. 4A, overexpression of Hsc70 significantly enhanced $2A^{pro}$-mediated IRES activity. Then, the interaction between $2A^{pro}$ and Hsc70 was investigated. By using the purified $2A^{pro}$ as a bait, a pull-down assay was performed and it was found that Hsc70 had a direct interaction with $2A^{pro}$. Please see FIG. 4B. It is demonstrated that IRES-driven translation was activated after the cleavage of eIF4G by $2A^{pro}$. We then checked the effect of Hsc70 on $2A^{pro}$ cleavage activity. As shown in FIG. 4C, the cleaved eIF4G was up-regulated in Hsc70 overexpressed cells, indicating an increase of $2A^{pro}$ proteolytic activity upon increased Hsc70 level. We then examined the effects of Hsc70 on $2A^{pro}$ regulated viral protein production upon viral infection. The si-Hsc70 was infected into the HEK 293T cell for forty-eight hours, then transfected the $2A^{pro}$ expression plasmid or empty vector and cultured for another twenty-four hours. Cells were finally infected with EV-A71 at an MOI of 5 for 9 hours. Consistent with previous findings, the viral protein markedly increased in the cells with ectopic expression of $2A^{pro}$ (please see FIG. 4D lane 1 vs lane 3); while $2A^{pro}$ failed to elicit the production of viral protein after knockdown of Hsc70 (please see FIG. 4D, lane 2 vs lane 4). This data suggested that Hsc70 is an important host factor to facilitate EV-A71 replication through regulating $2A^{pro}$ activity.

2.5 Hsc70 Inhibitor Ver-155008 Suppressed EV-A71 Infection

To address the drug target potential of Hsc70 against EV-A71, experiments were conducted to examine if Ver-155008, a chemical inhibitor of Hsc70, could protect cells from EV-A71 infection. In this regard, RD cells were pre-treated for 2 hours with Ver-155008, then infected the cells with EV-A71 for another 9 hours at an MOI of 10.

Figure 5A:
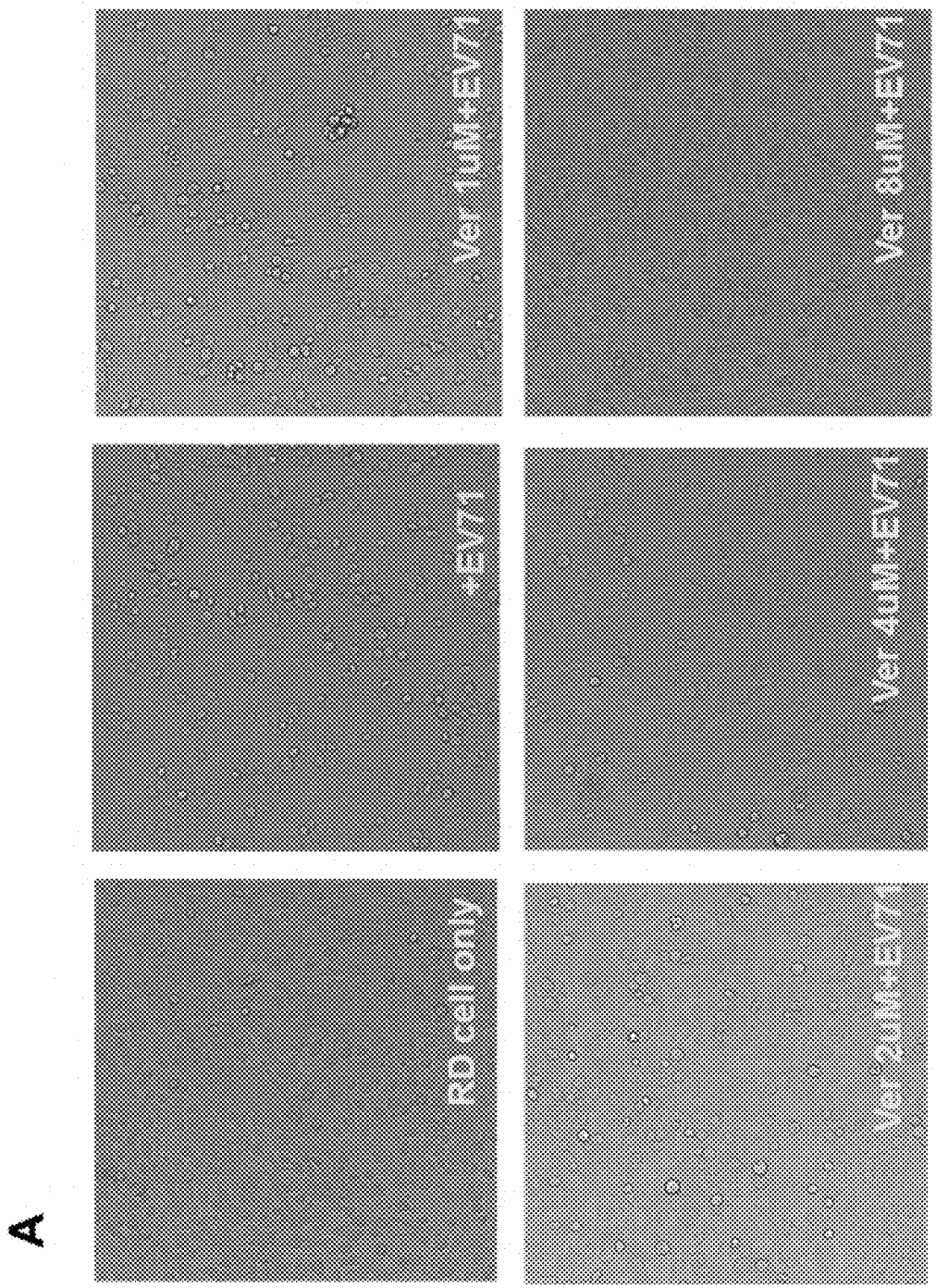
FIGS. 5A to 5D are representations showing small molecule inhibitor of Hsc70 reducing EV-A71 infection.
Figure 5B:
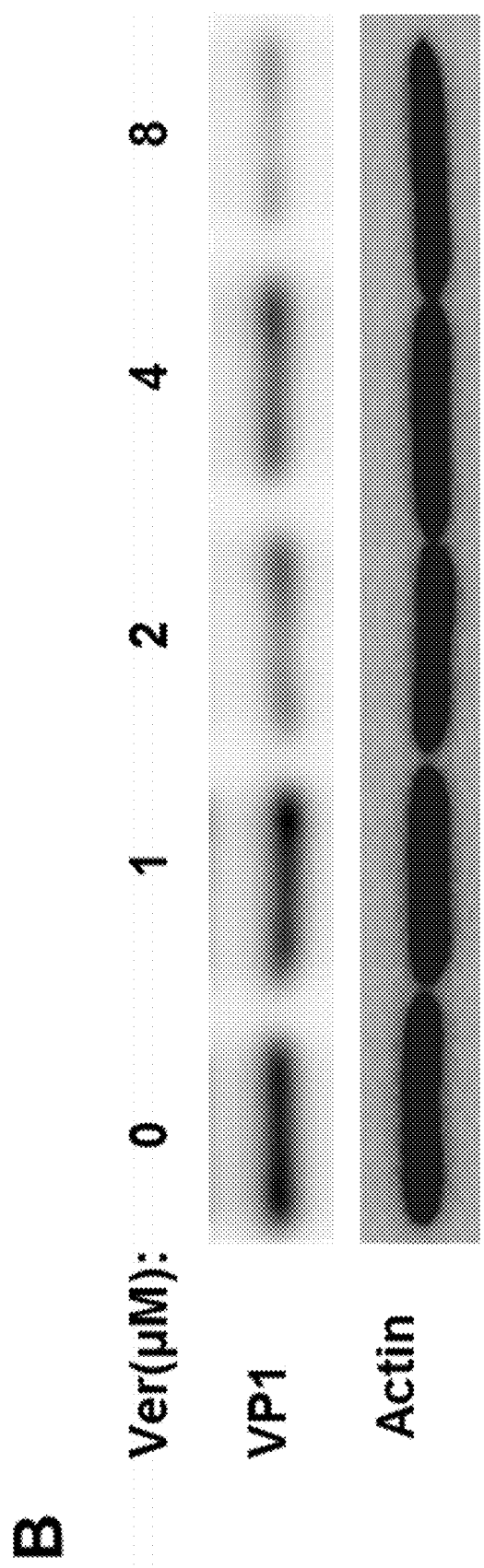
Figure 5C:
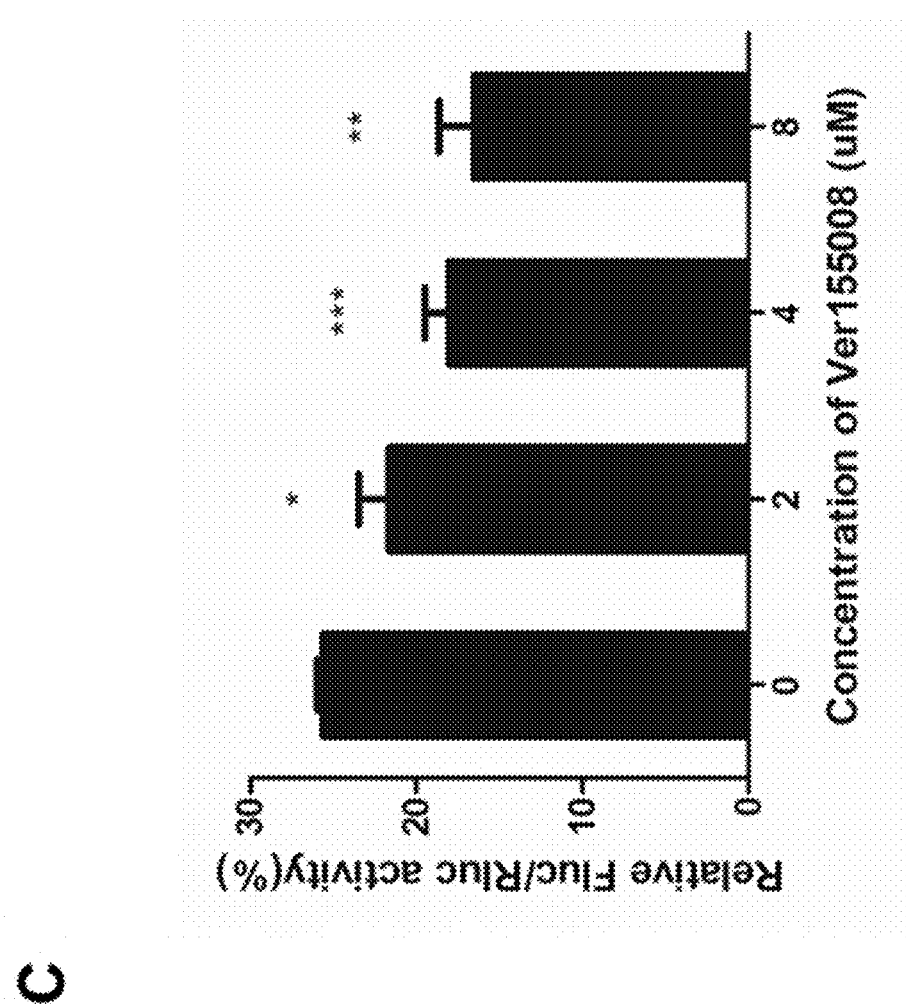
Figure 5D:
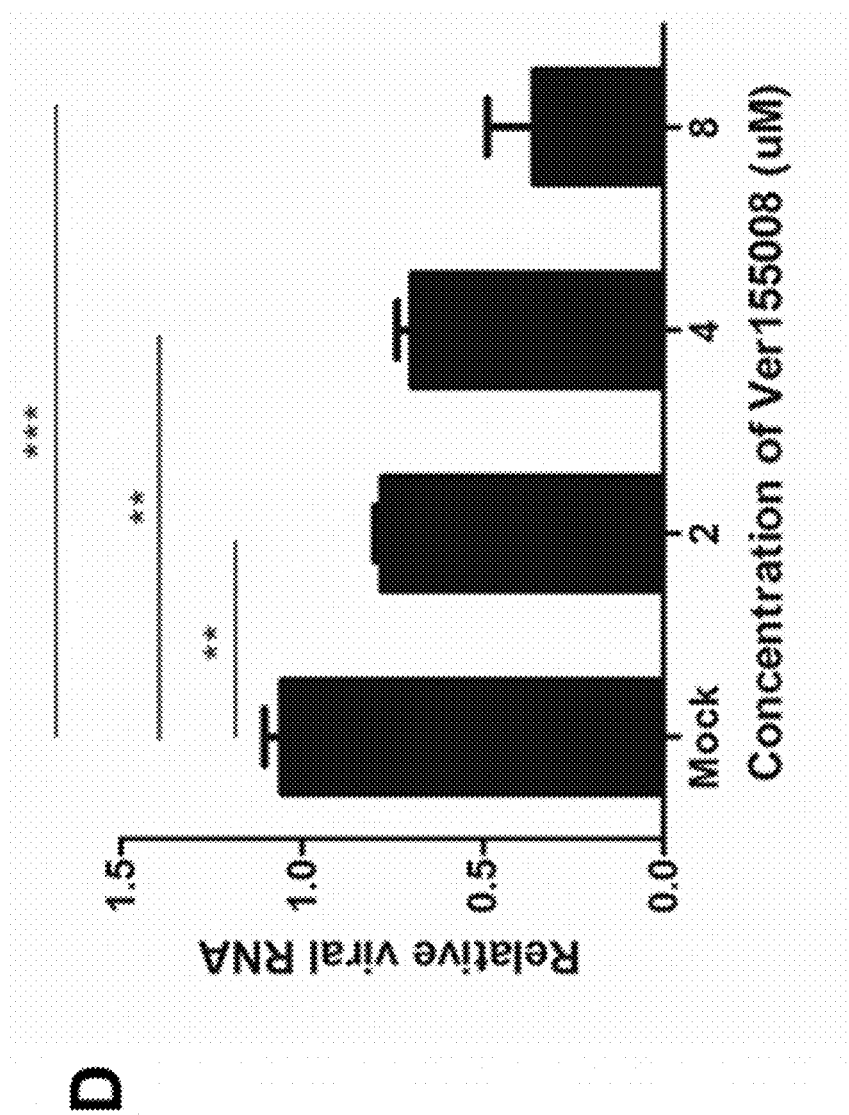

In FIG. 5A, cell images under light microscope. In FIG. 5B, proteins levels of VP0/2 by western blot are shown. In FIG. 5C, EV-A71 IRES activity detected by luciferase activities are shown. (n=3; ***, p<0.001). In FIG. 5D, there is shown the extracellular viral RNA levels were examined by qRT-PCR.

As shown in FIG. 5A, the control cells were healthy and tightly attached to the dishes while the infected cells were round and detached. The CPEs gradually declined with increased concentration of Ver-155008. There was nearly no obvious cytopathic effect at a concentration of 8 μM. The CC50 and IC50 were 47.67 μM and 2.01 μM, respectively. The selection index of Ver-155008 was 23.71 (Table 2). The viral VP1 levels was obviously repressed by Ver-155008 in a dose dependent manner. Please see FIG. 5B. More interestingly, the IRES activity also declined in a dose-dependent manner. Please see FIG. 5C. As expected, the secreted virions significantly decreased by 55% when the cells were treated with 8 μM of Ver-155008. Please see FIG. 5D.

3 Discussion

The above described studies have provided evidence to show Hsc70 as a positive regulator for viral infection such as EV-A71 infection. A mechanism was demonstrated that the Hsc70 up-regulated the IRES activity through enhancing $2A^{pro}$ mediated eIF4G cleavage. Most importantly, it is demonstrated that that Hsc70 inhibitor markedly repressed the EV-A71 infection and protected host cells from CPEs caused by EV-A71 infection, suggesting a potential therapeutic agent for combating EV-A71 infections.

Hsc70 is an extensively expressed protein located both in cytoplasm and nuclei. Previous studies have demonstrated the role of Hsc70 in many viral infections. During the infection of Rotavirus, a monoclonal antibody specific to Hsc70 blocks the virus infectivity. For influenza infection, Hsc70 binds to the viral protein, vRNP, to help the export of viral proteins from nuclei. Moreover, deletion of Hsc70 could inhibit HBV replication. However, the effect of Hsc70 on EV-A71 infection still keeps unclear. Other members of Hsp70 families have been shown important roles in EV-A71 infection. For example, recombinant Hsp78 could enhance the propagation of EV-A71 while knockdown of Hsp78 did not alter the viral yield. Here, for the first time, we report the positive role of Hsc70 in EV-A71 replication. It is demonstrated that depletion of Hsc70 obviously reduced EV-A71 infection. Please see FIGS. 1A to 1E. In contrast, ectopic expression of Hsc70 promoted the infection of EV-A71. Please see FIGS. 2A to 2E. This data suggests that Hsc70 is can an important antiviral target. Tests were then conducted to see if a chemical inhibitor of Hsc70 can also restrict EV-A71 infection. Ver-155008 shows a high potency to inhibit viral infectivity of EV-A71. Additionally, the low toxic in cell viability and high effect in viral restriction made it possible anti-viral drug against HFMD.

Figure 6:
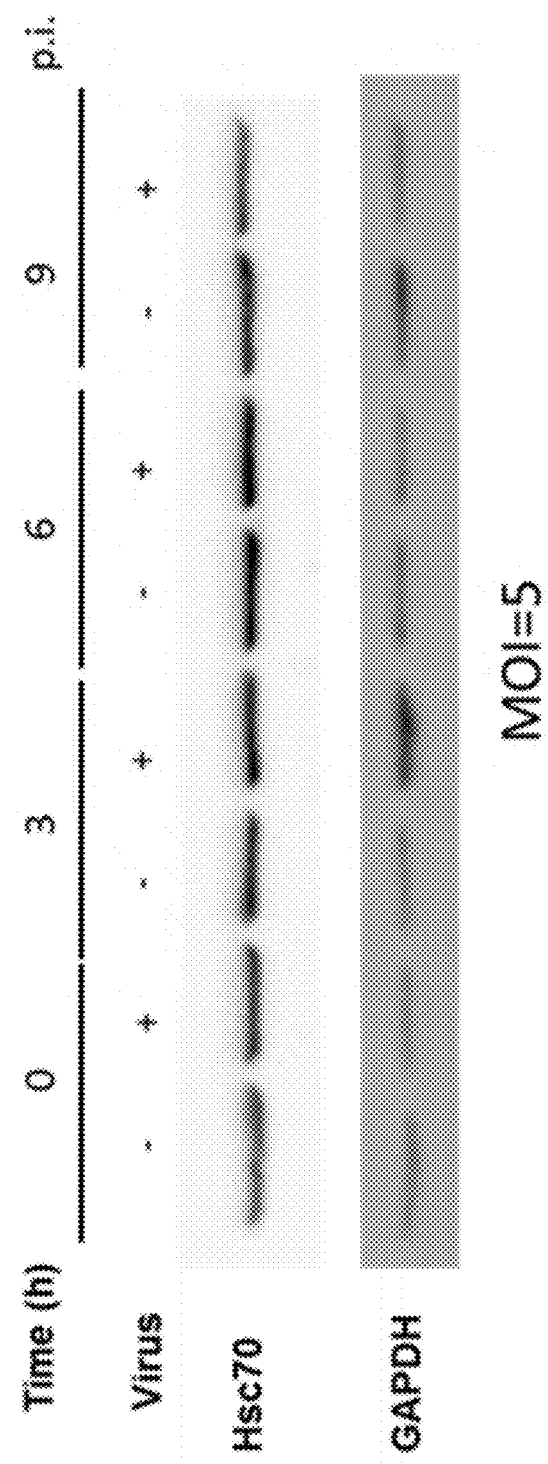
FIG. 6 is a representation showing apparent lack of stimulation of Hsc70 expression by EV-A71.

The IRES-driven translation was a key event for EV-A71 infection by generating the crucial proteins for viral RNA replication and production of viral proteins to gain viral progeny. In this study, there is shown that Hsc70 promoted the IRES activities by both gain- and loss-of-function studies. Please see FIGS. 3A to 3D. Oblongifolin M, a compound isolated from a traditional Chinese herb, represses EVA-71 infection by regulating the IRES activity via down-regulating ERp57 expression. However, it was shown that GRp78, another member of Hsp70 family, is upregulated during EV-A71 infection and displayed antiviral effects through activation of ER-stress signaling pathways. However, it appears that EV-A71 does not stimulate Hsc70 expression. Please see FIG. 6. This is reasonable because Hsc70 is one of the most abundant proteins in mammalian cells that is enough to facilitate virus activities after infection. In this study, there is shown that Hsc70 inhibitor inhibits the IRES activity to restrict the infection of EV-A71, suggesting that multiple heat shock proteins, involve in host response to EV-A71 infection that facilitating or restricting viral activity upon infection. Accordingly, different types of agonists or antagonists display either promoters or inhibitors of virus infections.

EV-A71 was found to recruit many host proteins to facilitate the IRES-driven translation through directly binding to the 5'-UTR of EV-A71. Our data reveals that Hsc70 can bind the full-length viral RNA of EV-A71. It would not be surprised because that Hsc70 would bind vRNP of influenza. However, our studies show that Hsc70 is not directly associated with the 5'-UTR. It is predictable that the bind on viral RNA genome would directly or indirectly employ certain regulations of viral activities, such as RNA replication, IRES-mediated translation or viral package. Besides the recruitment of host factors, the IRES-mediated translation can also be stimulated by viral proteins. $2A^{pro}$ is one of the notable proteases that can cleave elF4G, a key component for initiation of cap-dependent translation. After the cleavage, host cell translation machinery was obstructed which reduced competition of and eventually help viral translation. Moreover, the cleaved product of elF4G directly binds IRES and assisted the cap-independent translation. $2A^{pro}$ was well known to stimulate IRES mediated translation which depended on the enzymatic activity.

Our experiments shows that Hsc70 can interact with $2A^{pro}$. Furthermore, it is found that the cleavage activity of $2A^{pro}$ on elF4G was inhibited by Hsc70 knockdown, and the production of viral protein was strongly upregulated by $2A^{pro}$. Please see FIGS. 4A to 4D. However, this positive regulation was abolished after Hsc70 inhibition. This can partially explain why Hsc70 was not recruited to IRES but still stimulated the IRES activity. It is interesting whether SNPs of Hsc70 would affect EV-A71 infection and its sensitivity/resistance to Hsc70 inhibitors. Taken together, we demonstrated that Hsc70 was not working as an ITAF to promote IRES activity but through up-regulating $2A^{pro}$ activity.

In conclusion, Hsc70 exhibits a positive role in EV-A71 infection at least partly through enhancing IRES activity. Hsc70 inhibitors are thus therapeutic for antiviral in clinic settings.

It should be understood that certain features of the invention, which are, for clarity, described in the content of separate embodiments, may be provided in combination in a single embodiment. Conversely, various features of the invention which are, for brevity, described in the content of a single embodiment, may be provided separately or in any appropriate sub-combinations. It is to be noted that certain features of the embodiments are illustrated by way of non-limiting examples. It is also to be noted that certain features in connection with the invention are not explained in great detail for brevity reason. However, such features are readily understood by a skilled person in the art. Also, a skilled person in the art will be aware of the prior art which is not explained in the above for brevity purpose.

TABLE 1

Primer List.

| Gene | Sequences of primers |
| --- | --- |
| qRT-PCR primers | |
| EV-A71 positive strand RNA | F 5'-GCAGCCCAAAAGAACTTCAC-3' (SEQ ID NO: 3) R 5'-ATTTCAGCAGCTTGGAGTGC-3' (SEQ ID NO: 4) |
| EV-A71 negative strand RNA | F 5'-CGCATTGGGCGAGGTATC-3' (SEQ ID NO: 5) R 5'-CGGACTGTAGGCACCTCGAA-3' (SEQ ID NO: 6) |
| Hsc70 | F 5'-ACTCCAAGCTATGTCGCCTTT-3' (SEQ ID NO: 7) R 5'-TGGCATCAAAAACTGTGTTGGT-3' (SEQ ID NO: 8) |
| GAPDH | F 5'-GATTCCACCCATGGCAAATTCCA-3' (SEQ ID NO: 9) R 5'-TGGTGATGGGATTTCCATTGATGA-3' (SEQ ID NO: 10) |
| Cloning Primer | |
| $2A^{pro}$ | F 5'-CCGAATTCATGGGGAAATTTGGGCAACAG-3 (SEQ ID NO: 11) R 5'-GCACTCGAGCTGCTCCATAGCTTCTTC-3' (SEQ ID NO: 12) |

TABLE 2

The antiviral features of Hsc70 inhibitor Ver-155008

| Compound | Cytotoxicity | | Antiviral activity[a] | Selective Index |
|---|---|---|---|---|
| | CC50 (µM) | CC90 (µM) | IC50 (µM) | SI |
| Ver-155008 (HSC70 inhibitor) | 47.67 ± 0.34 | 91.92 ± 0.94 | 2.01 ± 0.05 | (CC50/IC50) 23.71 |

[a] RD cells were infected with EV-A71 at a MOI of 0.01 after treatment with serial dilution of Ver for 24 h.
[b] Values obtained from nonlinear regression analysis using SPSS 17.0.

REFERENCES

The following references are incorporated in their entirety and a skilled person is considered to be aware of disclosure of these references.

Böcking, T., Aguet, F., Harrison, S. C., Kirchhausen, T., 2011. Single-molecule analysis of a molecular disassemblase reveals the mechanism of Hsc70-driven clathrin uncoating. Nat Struct Mol Biol 18, 295-301.

Badorff, C., Lee, G. H., Lamphear, B. J., Martone, M. E., Campbell, K. P., Rhoads, R. E., Knowlton, K. U., 1999. Enteroviral protease 2A cleaves dystrophin: evidence of cytoskeletal disruption in an acquired cardiomyopathy. Nature medicine 5, 320-326.

Chang, L.-y., Lin, T.-y., Huang, Y-c., Tsao, K.-c., Shih, S.-r., Kuo, M.-I., Ning, H.-c., Chung, P.-w., Kang, C.-m., 1999. Comparison of enterovirus 71 and coxsackievirus A16 clinical illnesses during the Taiwan enterovirus epidemic, 1998. The Pediatric infectious disease journal 18, 1092-1096.

Chen, L. L., Kung, Y. A., Weng, K. F., Lin, J. Y., Horng, J. T., Shih, S. R., 2013. Enterovirus 71 infection cleaves a negative regulator for viral internal ribosomal entry site-driven translation. J Virol 87, 3828-3838.

Chuang, C.-K., Yang, T.-H., Chen, T.-H., Yang, C.-F., Chen, W.-J., 2015. Heat shock cognate protein 70 isoform D is required for clathrin-dependent endocytosis of Japanese encephalitis virus in C6/36 cells. Journal of General Virology 96, 793-803.

Chung, S.-K., Kim, J.-Y, Kim, I.-B., Park, Paek, K.-H., Nam, J.-H., 2005. Internalization and trafficking mechanisms of coxsackievirus B3 in HeLa cells. Virology 333, 31-40.

Duan, H., Zhu, M., Xiong, Q., Wang, Y, Xu, C., Sun, J., Wang, C., Zhang, H., Xu, P., Peng, Y, 2017. Regulation of enterovirus 2A protease-associated viral IRES activities by the cell's ERK signaling cascade: Implicating ERK as an efficiently antiviral target. Antiviral Res 143, 13-21.

Gao, M., Duan, H., Liu, J., Zhang, H., Wang, X., Zhu, M., Guo, J., Zhao, Z., Meng, L., Peng, Y, 2014. The multitargeted kinase inhibitor sorafenib inhibits enterovirus 71 replication by regulating IRES-dependent translation of viral proteins. Antiviral research 106, 80-85.

Ho, M., Chen, E.-R., Hsu, K.-H., Twu, S.-J., Chen, K.-T., Tsai, S.-F., Wang, J.-R., Shih, S.-R., 1999. An Epidemic of Enterovirus 71 Infection in Taiwan. New England Journal of Medicine 341, 929-935.

Hu, J. J., Song, W., Zhang, S. D., Shen, X. H., Qiu, X. M., Wu, H. Z., Gong, P. H., Lu, S., Zhao, Z. J., He, M. L., Fan, H., 2016. HBx-upregulated lncRNA UCA1 promotes cell growth and tumorigenesis by recruiting EZH2 and repressing p27Kip1/CDK2 signaling. Scientific reports 6, 23521.

Huang, C.-C., Liu, C.-C., Chang, Y-C., Chen, C.-Y, Wang, S.-T., Yeh, T.-F., 1999. Neurologic Complications in Children with Enterovirus 71 Infection. New England Journal of Medicine 341, 936-942.

Huang, H.-I., Weng, K.-F., Shih, S.-R., 2012. Viral and host factors that contribute to pathogenicity of enterovirus 71. Future microbiology 7, 467-479.

Huang, H. I., Chang, Y Y, Lin, J. Y., Kuo, R. L., Liu, H. P., Shih, S. R., Wu, C. C., 2016. Interactome analysis of the EV71 5' untranslated region in differentiated neuronal cells SH-SY5Y and regulatory role of FBP3 in viral replication. Proteomics 16, 2351-2362.

Hung, C.-T., Kung, Y-A., Li, M.-L., Brewer, G., Lee, K.-M., Liu, S.-T., Shih, S.-R., 2016. Additive promotion of viral internal ribosome entry site-mediated translation by Far Upstream Element-Binding Protein 1 and an Enterovirus 71-induced cleavage product. PLoS pathogens 12, e1005959.

Hunt, S. L., Skern, T., Liebig, H. D., Kuechler, E., Jackson, R. J., 1999. Rhinovirus 2A proteinase mediated stimulation of rhinovirus RNA translation is additive to the stimulation effected by cellular RNA binding proteins. Virus research 62, 119-128.

Jheng, J.-R., Wang, S.-C., Jheng, C.-R., Horng, J.-T., 2016. Enterovirus 71 induces dsRNA/PKR-dependent cytoplasmic redistribution of GRP78/BiP to promote viral replication. Emerging microbes & infections 5, e23.

Kung, Y A., Hung, C. T., Chien, K. Y, Shih, S. R., 2017. Control of the negative IRES trans-acting factor KHSRP by ubiquitination. Nucleic Acids Res 45, 271-287.

Lee, K. M., Chen, C. J., Shih, S. R., 2017. Regulation Mechanisms of Viral IRES-Driven Translation. Trends in microbiology 25, 546-561.

Lin, J.-Y, Li, M.-L., Huang, P.-N., Chien, K.-Y, Horng, J.-T., Shih, S.-R., 2008. Heterogeneous nuclear ribonuclear protein K interacts with the enterovirus 71 5' untranslated region and participates in virus replication. Journal of General Virology 89, 2540-2549.

Lin, J.-Y, Shih, S.-R., Pan, M., Li, C., Lue, C.-F., Stollar, V., Li, M.-L., 2009. hnRNP A1 interacts with the 5' untranslated regions of enterovirus 71 and Sindbis virus RNA and is required for viral replication. Journal of virology 83, 6106-6114.

Lu, J., Yi, L., Zhao, J., Yu, J., Chen, Y, Lin, M. C., Kung, H.-F., He, M.-L., 2012. Enterovirus 71 disrupts interferon signaling by reducing the level of interferon receptor 1. Journal of virology 86, 3767-3776.

Ma, Y, Yu, J., Chan, H. L., Chen, Y C., Wang, H., Chen, Y, Chan, C. Y, Go, M. Y., Tsai, S. N., Ngai, S. M., To, K. F., Tong, J. H., He, Q. Y, Sung, J. J., Kung, H. F., Cheng, C. H., He, M. L., 2009. Glucose-regulated protein 78 is an intracellular antiviral factor against hepatitis B virus. Molecular & cellular proteomics: MCP 8, 2582-2594.

McMinn, P. C., 2002. An overview of the evolution of enterovirus 71 and its clinical and public health significance. FEMS microbiology reviews 26, 91-107.

Ohlmann, T., Rau, M., Pain, V. M., Morley, S. J., 1996. The C-terminal domain of eukaryotic protein synthesis initiation factor (eIF) 4G is sufficient to support cap-independent translation in the absence of eIF4E. The EMBO journal 15, 1371-1382.

Pérez-Vargas, J., Romero, P., López, S., Arias, C. F., 2006. The peptide-binding and ATPase domains of recombinant hsc70 are required to interact with rotavirus and reduce its infectivity. Journal of virology 80, 3322-3331.

Salinas, E., Byrum, S. D., Moreland, L. E., Mackintosh, S. G., Tackett, A. J., Forrest, J. C., 2016. Identification of Viral and Host Proteins That Interact with Murine Gammaherpesvirus 68 Latency-Associated Nuclear Antigen during Lytic Replication: a Role for Hsc70 in Viral Replication. Journal of virology 90, 1397-1413.

Sanz, M. A., Welnowska, E., Redondo, N., Carrasco, L., 2010. Translation driven by picornavirus IRES is hampered from Sindbis virus replicons: rescue by poliovirus 2A protease. Journal of molecular biology 402, 101-117.

Schmidt, N. J., Lennette, E. H., Ho, H. H., 1974. An apparently new enterovirus isolated from patients with disease of the central nervous system. The Journal of infectious diseases 129, 304-309.

Stricher, F., Macri, C., Ruff, M., Muller, S., 2013. HSPA8/HSC70 chaperone protein: structure, function, and chemical targeting. Autophagy 9, 1937-1954.

Sztuba-Solinska, J., Diaz, L., Kumar, M. R., Kolb, G., Wiley, M. R., Jozwick, L., Kuhn, J. H., Palacios, G., Radoshitzky, S. R., J. Le Grice, S. F., 2016. A small stem-loop structure of the Ebola virus trailer is essential for replication and interacts with heat-shock protein A8. Nucleic acids research 44, 9831-9846.

Thompson, S. R., Sarnow, P., 2003. Enterovirus 71 contains a type I IRES element that functions when eukaryotic initiation factor eIF4G is cleaved. Virology 315, 259-266.

Wang, M., Dong, Q., Wang, H., He, Y, Chen, Y, Zhang, H., Wu, R., Chen, X., Zhou, B., He, J., Kung, H. F., Huang, C., Wei, Y, Huang, J. D., Xu, H., He, M. L., 2016. Oblongifolin M, an active compound isolated from a Chinese medical herb *Garcinia oblongifolia*, potently inhibits enterovirus 71 reproduction through downregulation of ERp57. Oncotarget 7, 8797-8808.

Wang, S.-M., Liu, C.-C., 2014. Update of enterovirus 71 infection: epidemiology, pathogenesis and vaccine. Expert Review of Anti-infective Therapy 12, 447-456.

Wang, Y-P., Liu, F., He, H.-W., Han, Y-X., Peng, Z.-G., Li, B.-W., You, X.-F., Song, D.-Q., Li, Z.-R., Yu, L.-Y, 2010. Heat stress cognate 70 host protein as a potential drug target against drug resistance in hepatitis B virus. Antimicrobial agents and chemotherapy 54, 2070-2077.

Wang, Y, Zou, G., Xia, A., Wang, X., Cai, J., Gao, Q., Yuan, S., He, G., Zhang, S., Zeng, M., 2015. Enterovirus 71 infection in children with hand, foot, and mouth disease in Shanghai, China: epidemiology, clinical feature and diagnosis. Virology journal 12, 83.

Watanabe, K., Fuse, T., Asano, I., Tsukahara, F., Maru, Y, Nagata, K., Kitazato, K., Kobayashi, N., 2006. Identification of Hsc70 as an influenza virus matrix protein (M1) binding factor involved in the virus life cycle. FEBS letters 580, 5785-5790.

Watanabe, K., Takizawa, N., Noda, S., Tsukahara, F., Maru, Y, Kobayashi, N., 2008a. Hsc70 regulates the nuclear export but not the import of influenza viral RNP: A possible target for the development of anti-influenza virus drugs. Drug Discov Ther 2, 77-84.

Watanabe, K., Takizawa, N., Noda, S., Tsukahara, F., Maru, Y, Kobayashi, N., 2008b. Hsc70 regulates the nuclear export but not the import of influenza viral RNP: A possible target for the development of anti-influenza virus drugs. Drug discoveries & therapeutics 2, 77-84.

Yi, L., Lu, J., Kung, H. F., He, M. L., 2011. The virology and developments toward control of human enterovirus 71. Critical reviews in microbiology 37, 313-327.

Zárate, S., Cuadras, M. A., Espinosa, R., Romero, P., Juárez, K. O., Camacho-Nuez, M., Arias, C. F., López, S., 2003. Interaction of rotaviruses with Hsc70 during cell entry is mediated by VP5. Journal of virology 77, 7254-7260.

Zhang, H., Song, L., Cong, H., Tien, P., 2015. Nuclear protein Sam68 interacts with the enterovirus 71 internal ribosome entry site and positively regulates viral protein translation. Journal of virology 89, 10031-10043.

Zhu, B., Xu, T., Lin, Z., Wang, C., Li, Y, Zhao, M., Hua, L., Xiao, M., Deng, N., 2017. Recombinant heat shock protein 78 enhances enterovirus 71 propagation in Vero cells and is induced in SK—N—SH cells during the infection. Archives of Virology 162, 1649-1660.

Ziegler, E., Borman, A. M., Deliat, F. G., Liebig, H. D., Jugovic, D., Kean, K. M., Skern, T., Kuechler, E., 1995. Picornavirus 2A proteinase-mediated stimulation of internal initiation of translation is dependent on enzymatic activity and the cleavage products of cellular proteins. Virology 213, 549-557.

Wang Y, Lee S, Ha Y, Lam W, Chen S R, Dutschman G E, Gullen E A, Grill S P, Cheng Y, FUrstner A, Francis S, Baker D C, Yang X, Lee K H, Cheng Y C. Tylophorine Analogs Allosterically Regulates Heat Shock Cognate Protein 70 And Inhibits Hepatitis C Virus Replication. Sci Rep. 2017 Aug. 30; 7(1):10037.

The invention claimed is:

1. A method of treatment of enterovirus A71 infection in a subject, comprising a step of administering an effective amount of a Hsc70 inhibitor to the subject in need thereof, wherein the Hsc70 inhibitor is Ver-155008.

2. A method for modulating activity of enterovirus A71 in a subject, comprising a step of administering an effective amount of a Hsc70 inhibitor in the subject in need thereof, wherein the Hsc70 inhibitor is Ver-155008.

3. A method as claimed in claim 2, wherein the modulating is inhibiting the activity of the enterovirus A71 in the subject.

* * * * *